(12) United States Patent
Altshuler

(10) Patent No.: US 6,508,813 B1
(45) Date of Patent: Jan. 21, 2003

(54) SYSTEM FOR ELECTROMAGNETIC RADIATION DERMATOLOGY AND HEAD FOR USE THEREWITH

(75) Inventor: Gregory Altshuler, Wilmington, MA (US)

(73) Assignee: Palomar Medical Technologies, Inc., Burlington, MA (US)

( * ) Notice: Subject to any disclaimer, the term of this patent is extended or adjusted under 35 U.S.C. 154(b) by 0 days.

(21) Appl. No.: 09/268,433

(22) Filed: Mar. 12, 1999

Related U.S. Application Data

(63) Continuation-in-part of application No. 08/759,036, filed on Dec. 2, 1996, now Pat. No. 6,015,404, and a continuation-in-part of application No. 08/759,136, filed on Dec. 2, 1996, now abandoned, and a continuation-in-part of application No. 09/078,055, filed on May 13, 1998, now Pat. No. 6,273,884.

(60) Provisional application No. 60/077,794, filed on Mar. 12, 1998, and provisional application No. 60/115,447, filed on Jan. 8, 1999.

(51) Int. Cl.$^7$ .......................... A61B 18/18; A61N 5/067
(52) U.S. Cl. .............................. 606/9; 606/16; 606/17; 607/89
(58) Field of Search ............................ 606/3, 9, 10, 11, 606/13, 14, 15, 16, 17; 219/121; 607/88–89, 100

(56) References Cited

U.S. PATENT DOCUMENTS 3,327,712 A    6/1967    Kaufman (List continued on next page.)

FOREIGN PATENT DOCUMENTS

| AT | AT 400 305 B | 12/1995 |
|---|---|---|
| DE | 3837248 A | 5/1990 |
| EP | 0 142 671 | 5/1985 |
| EP | 0 565 331 | 10/1993 |
| EP | 0 724 894 | 8/1996 |
| EP | 0 726 083 | 8/1996 |
| EP | 0 736 308 | 10/1996 |

(List continued on next page.)

OTHER PUBLICATIONS

Altshuler, Gregory B., et al., "Acoustic response of hard dental tissues to pulsed laser action," *SPIE*, vol. 2080, Dental Applications of Laser (1993), pp. 97–103.

(List continued on next page.)

*Primary Examiner*—Roy Gibson
(74) *Attorney, Agent, or Firm*—Wolf, Greenfield, & Sacks, P.C.

(57) ABSTRACT

A system for treating a selected dermatologic problem and a head for use with such system are provided. The head may include an optical waveguide having a first end to which EM radiation appropriate for treating the condition is applied. The waveguide also has a skin-contacting second end opposite the first end, a temperature sensor being located within a few millimeters, and preferably within 1 to 2 millimeters, of the second end of the waveguide. A temperature sensor may be similarly located in other skin contacting portions of the head. A mechanism is preferably also provided for removing heat from the waveguide and, for preferred embodiments, the second end of the head which is in contact with the skin has a reflection aperture which is substantially as great as the radiation back-scatter aperture from the patient's skin. Such aperture may be the aperture at the second end of the waveguide or a reflection plate or surface of appropriate size may surround the waveguide or other light path at its second end. The portion of the back-scattered radiation entering the waveguide is substantially internally reflected therein, with a reflector being provided, preferably at the first end of the waveguide, for returning back-scattered light to the patient's skin. The reflector may be angle dependent so as to more strongly reflect back scattered light more perpendicular to the skin surface than back scattered radiation more parallel to the skin surface. Controls are also provided responsive to the temperature sensing for determining temperature at a predetermined depth in the patient's skin, for example at the DE junction, and for utilizing this information to detect good thermal contact between the head and the patient's skin and to otherwise control treatment. The head may also have a mechanism for forming a reflecting chamber under the waveguide and drawing a fold of skin therein, or for providing a second enlarged waveguide to expand the optical aperture of the radiation.

50 Claims, 10 Drawing Sheets

U.S. PATENT DOCUMENTS

| | | |
|---|---|---|
| 3,527,932 A | 9/1970 | Thomas |
| 3,538,919 A | 11/1970 | Meyer |
| 3,622,743 A | 11/1971 | Muncheryan |
| 3,693,623 A | 9/1972 | Harte et al. |
| 3,834,391 A | 9/1974 | Block |
| 3,900,034 A | 8/1975 | Katz et al. |
| 4,233,493 A | 11/1980 | Nath |
| 4,273,109 A * | 6/1981 | Enderby .................. 219/121 |
| 4,316,467 A | 2/1982 | Muckerheide |
| 4,388,924 A | 6/1983 | Weissman et al. |
| 4,461,294 A | 7/1984 | Baron |
| 4,539,987 A | 9/1985 | Nath et al. |
| 4,608,978 A | 9/1986 | Rohr |
| 4,617,926 A | 10/1986 | Sutton |
| 4,695,697 A * | 9/1987 | Kosa ........................ 219/121 |
| 4,718,416 A | 1/1988 | Nanaumi |
| 4,733,660 A | 3/1988 | Itzkan |
| 4,747,660 A | 5/1988 | Nishioka |
| 4,819,669 A | 4/1989 | Politzer |
| 4,832,024 A | 5/1989 | Boussignac |
| 4,860,172 A | 8/1989 | Schlager et al. |
| 4,860,744 A | 8/1989 | Johnson et al. |
| 4,917,084 A | 4/1990 | Sinofsky |
| 4,926,227 A | 5/1990 | Jensen |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,282,797 A | 2/1994 | Chess |
| 5,300,097 A | 4/1994 | Lerner et al. |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A * | 9/1994 | Ghaffari ..................... 606/9 |
| 5,348,551 A | 9/1994 | Spears et al. |
| 5,350,376 A | 9/1994 | Brown |
| 5,380,317 A | 1/1995 | Everett et al. |
| 5,405,368 A | 4/1995 | Eckhouse |
| 5,415,654 A | 5/1995 | Daikuzono |
| 5,425,728 A | 6/1995 | Tankovich |
| 5,474,549 A | 12/1995 | Ortiz et al. |
| 5,486,172 A | 1/1996 | Chess |
| 5,505,726 A | 4/1996 | Meserol |
| 5,519,534 A | 5/1996 | Smith et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,662,643 A * | 9/1997 | Kung et al. ................. 606/3 |
| 5,662,644 A | 9/1997 | Swor |
| 5,683,380 A | 11/1997 | Eckhouse |
| 5,698,866 A | 12/1997 | Doiron et al. |
| 5,735,844 A | 4/1998 | Anderson et al. |
| 5,735,884 A | 4/1998 | Thompson et al. |
| 5,743,901 A | 4/1998 | Grove et al. |
| 5,755,751 A | 5/1998 | Eckhouse |
| 5,759,200 A | 6/1998 | Azar |
| 5,782,249 A | 7/1998 | Weber et al. |
| 5,810,801 A | 9/1998 | Anderson et al. |
| 5,820,626 A * | 10/1998 | Baumgardner ............... 606/13 |
| 5,824,023 A | 10/1998 | Anderson |
| 5,828,803 A | 10/1998 | Eckhouse |
| 5,830,208 A | 11/1998 | Muller |
| 5,836,999 A | 11/1998 | Eckhouse |
| 5,849,029 A * | 12/1998 | Eckhouse ................... 607/104 |
| 5,853,407 A | 12/1998 | Miller |
| 5,885,211 A * | 3/1999 | Eppstein et al. ............ 600/309 |
| 5,885,273 A | 3/1999 | Eckhouse et al. |
| 5,885,274 A | 3/1999 | Fullmer et al. |
| 5,944,748 A | 8/1999 | Mager et al. |
| 5,948,011 A | 9/1999 | Knowlton ................... 607/101 |
| 5,954,710 A | 9/1999 | Paolini et al. |
| 5,964,749 A | 10/1999 | Eckhouse et al. |
| 5,968,033 A | 10/1999 | Fuller |
| 5,968,034 A | 10/1999 | Fullmer et al. |
| 6,015,404 A | 1/2000 | Altshuler et al. |
| 6,027,495 A | 2/2000 | Miller |
| RE36,634 E | 3/2000 | Ghaffari |
| 6,050,990 A | 4/2000 | Tankovich et al. |
| 6,056,738 A | 5/2000 | Marchitto et al. |
| 6,059,820 A | 5/2000 | Baronov |
| 6,080,146 A | 6/2000 | Altshuler et al. |
| 6,069,029 A | 8/2000 | O'Donnell, Jr. ................ 606/9 |
| 6,096,029 A | 8/2000 | O'Donnell, Jr. |
| 6,096,209 A | 8/2000 | O'Brien et al. |
| 6,120,497 A | 9/2000 | Anderson |
| 6,149,644 A | 11/2000 | Xie |
| 6,174,325 B1 | 1/2001 | Eckhouse |
| 6,197,020 B1 | 3/2001 | O'Donnell |
| 6,273,884 B1 | 8/2001 | Altshuler et al. |
| 6,280,438 B1 | 8/2001 | Eckhouse |

FOREIGN PATENT DOCUMENTS

| | | |
|---|---|---|
| EP | 0 755 698 | 1/1997 |
| EP | 0 763 371 | 3/1997 |
| EP | 0 765 673 | 4/1997 |
| EP | 0 765 674 | 4/1997 |
| EP | 0 783 904 A2 | 7/1997 |
| FR | 2 591 902 | 6/1987 |
| FR | 2 591 902 | 7/1987 |
| GB | 2 044 908 A | 10/1980 |
| GB | 2 123 287 A | 2/1982 |
| RU | 95105406 | 6/1997 |
| RU | 94012665 | 9/1997 |
| RU | 94040344 | 9/1997 |
| RU | 95102749 | 11/1997 |
| RU | 4954402 | 12/1998 |
| SU | 532304 | 7/1974 |
| SU | 719439 | 8/1975 |
| SU | 741747 | 10/1977 |
| SU | 1257475 A1 | 9/1986 |
| SU | 1326962 A1 | 7/1987 |
| WO | WO 0 142 671 | 9/1984 |
| WO | WO 86/02783 | 5/1986 |
| WO | WO 90/00420 | 1/1990 |
| WO | WO 92/16338 | 10/1992 |
| WO | WO 92/19165 | 11/1992 |
| WO | WO 93/05920 A1 | 4/1993 |
| WO | WO 95/15725 A1 | 6/1995 |
| WO | WO 95/32441 A1 | 11/1995 |
| WO | WO 95/32441 | 11/1995 |
| WO | WO 96/23447 A1 | 8/1996 |
| WO | WO 96/25979 A1 | 8/1996 |
| WO | WO 97/13458 | 4/1997 |
| WO | WO 98/04317 | 2/1998 |

| | | |
|---|---|---|
| WO | WO 98/24507 | 6/1998 |
| WO | WO 98/51235 A1 | 11/1998 |
| WO | WO 98/52481 A1 | 11/1998 |
| WO | WO 99/29243 A1 | 6/1999 |
| WO | WO 99/38569 A3 | 8/1999 |
| WO | WO 99/38569 A2 | 8/1999 |
| WO | WO 99/46005 A1 | 9/1999 |
| WO | WO 00/03257 A1 | 1/2000 |
| WO | WO 01/03257 A1 | 1/2001 |
| WO | WO 01/34048 | 5/2001 |

OTHER PUBLICATIONS

Altshuler, G. B., et al., "Extended Theory of Selective Photothermolysis," *Lasers in Surgery and Medicine*, 29: 416–432 (2001).

Amy, Robert L. and Storb, R., "Selective Mitochondrial Damage by a Ruby Laser Microbeam: An Electron Microscopic Study," *Science*, 15:756–758, Nov. 1965.

Anderson, R. R, and Parrish, J. A., M.D., "Selective Photothermolysis: Precise Microsurgery by Selective Absorption of Pulsed Radiation," *Science*, 220:524–527, 1983.

Belikov, A.V., et al., "Identification of enamel and dentine under tooth laser treatment," *SPIE*, Progress in Biomedical Optics, Europt Series, Proceedings of Medical Applications of Lasers III, vol. 2623, pp. 109–116.

Dover, J. S., et al., "Pigmented Guinea Pig Skin Irradiated with Q–Switched Ruby Laser Pulses," *Arch Dermatol*, 125:43–49, 1989.

Finkelstein, L. H. and Blatstein, Lee M., "Epilation of Hair–Bearing Urethal Grafts Using the Neodymium: YAG Surgical Laser," *The Journal of Urology*, 146:840–842, 1991.

Goldman, L., "Laser History and Theory," "Laser Instrumentation," and "Summary and Conclusions," Biomedical Aspects of the Laser, New York, Springer–Verlag, 1967, pp. iii–11, 220–232.

Goldman L., "Dermatologic Manifestation of Laser Radiation," *Fed Am Soc Exp Biology*, Suppl. 14:S–92 — S–93, 1965.

Goldman, L., "Effects of New Laser Systems on the Skin," *Arch Dermatol*, 108: 385–390, 1973.

Goldman, L., "Laser Surgery for Skin Cancer," *NY State J Med*, 77:1897–1900, 1977.

Goldman, L., "Surgery by Laser for Malignant Melanoma," *J. Dermatol. Surg. Oncol.*. 5(2):141–144, 1979.

Goldman, L., "The Skin," *Arch Environ Health*, 18:434–426, 1969.

Goldman, L. and Richfield, D. F., "The Effect of Repeated Exposures to Laser Beams," *Acta Derm.–Veneoral*, 44:264–268, 1964.

Goldman, L. and Rockwell, J., "Laser Action at the Cellular Level,"*JAMA*, 198:641–644, 1966.

Goldman, L. and Wilson, R. G., "Treatment of Basal Cell Epithelioma by Laser Radiation," *JAMA*, 189:773–775, 1964.

Goldman, L., et al., "Biomedical Aspects of Lasers,"*JAMA*, 188:230–234, 1964.

Goldman, L., et al., "Effect of the Laser Beam on the Skin: Preliminary and Short Report," *The Journal of Investigative Dermatology*, 40:121–122, 1963.

Goldman, L., et al., "The Effect of the Laser Beam on the Skin III. Exposure of Cytological Preparations," *The Journal of Investigative Dermatology*, 42:247–251, 1964.

Goldman, L., et al., "Impact of the Laser on Nevi and Melanomas," *Arch Dermatol*, 90:71–75, 1964.

Goldman, L., et al., "Laser Treatment of Tattoos," *JAMA*, 210:163–166, 1967.

Goldman, L., et al.,"Long–Term Laser Exposure of a Senile Freckle," *Arch Environ Health*, 22:401–403, 1971.

Goldman, L., et al., "Pathology of the Effect of the Laser Beam on the Skin," *Nature*, 197:912–914, 1963.

Goldman, L., et al., "Preliminary Investigation of fat Embolization from Pulsed Ruby Laser Impacts of Bone," *Nature*, 221:361–363, 1969.

Goldman, L., et al., "Radiation from a Q–Switched Ruby Laser. Effect of Repeated Impacts of Power Output of 10 Megawatts on a Tattoo of Man," *The Journal of Investigative Dermatology*, 44:69–71, 1965.

Goldman, L., et al., "Replica Microscopy and Scanning Electron Microsopy of Lawer Impacts on the Skin," *The Journal of Investigative Dermatology*, 52:18–24, 1969.

Grossman, M. C., et al., "Damage to Hair Follicles by Normal–mode Ruby Laser Pulses,"*Journal of the American Academy of Dermatology*, 35(6):889–894, 1996.

Grossman, M. C., et al., "Laser Targeted at Hair Follicles," *Lasers Med Surg.*, Suppl. 7:221, 1995.

Klein, E., et al., "Biological Effects of Laser Radiation I: Threshold Studies and Reversible Depigmentation in Rodent Skin, " *Northeast Electronics Research and Engineering Meeting — NEREM Record* – 1965, IEEE Catalog No. F–60, (Nov. 4, 1965) pp. 108–109.

Kuhns, J. G., et al., "Biological Effects of Laser Radiation II: Effects of Laser Irradiation on the Skin," *Northeast Electronics Research and Engineering Meeting — NEREM Record* 1965, IEEE Catalogue No. F–60, (Nov. 4, 1965) pp. 152–153.

Kuhns, James G., et al., "Laser Injury in Skin," *Laboratory Investigation*, vol. 17, No. 1, (Jul., 1967) pp. 1–13.

Manstein, Dieter, et al., "Selective Photothermolysis of Lipid–Rich Tissue," *American Society for Laser Medicine and Surgery Abstracts*, No. 17, American Society for Laser Medicine and Surgery Twenty–First Annual Meeting, Apr. 20–22, 2001, p. 6.

Margolis, R. J., et al., "Visible Action Spectrum for Melanin–Specific Selective Photothermolysis," *Lasers in Surgery and Medicine*, 9:389–397, 1989.

Parrish, J. A., M.D., et al., "Selective Thermal Effects with Pulsed Irradiation from Lasers: From Organ to Organelle," *The Journal of Investigative Dermatology*, 80:75s–80s, 1983.

Polla, L. L., et al., "Melanosomes Are a Primary Target of Q–Switched Ruby Laser Irradiation in Guinea Pig Skin," *The Journal of Investigative Dermatology*, 89:281–286, 1987.

Shimbashi, T. and Kojima, T., "Ruby Laser Treatment of Pigmented Skin Lesions," *Aesthetic Plastic Surgery*, 19:225–229, 1995.

Stratton, K., et al., "Biological Effects of Laser Radiation II: ESR Studies of Melanin Containing Tissues after Laser Irradiation,"*Northeast Electronics Research and Engineering Meeting —NEREM Record* – 1965, IEEE Catalogue No. F–60, (Nov. 4, 1965) pp. 150–151.

Taylor, C. R., et al., "Treatment of Tattoos by Q–Switched Ruby Laser," *Arch Dermatol*, 126:893–899, 1990.

Tuchin, Valery V., "Laser Light Scattering in Biomedical Diagnostics and Therapy" reprinted from *Journal of Laser Applications*, vol. 5(2,3), pp. 43–60 (Fall 1993) Laser Institute of America, Toledo, Ohio.

Watanabe, S., et al., "Comparative Studies of Femtosecond to Microsecond Laser Pulses on Selective Pigmented Cell Injury in Skin," *Photochemistry and Photobiology*, 53:757–762, 1991.

Watanabe, S., et al., The Effect of Pulse Duration on Selective Pigmented Cell Injury by Dye Lasers, *The Journal of Investigative Dermatology*, 88:523, 1987.

Welch, A. J., et al., "Evaluation of Cooling Techniques for the Protection of the Epidermis during ND–YAG Laser Irradiation of the Skin,"*Neodymiun–YAG Laser in Medicine and Surgery*. New York, Elsevier, 1983, pp. 196–204.

Yules, R. B., et al., "The Effect of Q–Switched Ruby Laser Rediation on Dermal Tattoo Pigment in Man," *Arch Surg*, 95:179–180, 1967.

Zeitler, E. and Wolbarsht, M. L., "Laser Charasteristics that Might be Useful in Biology," *Laser Applications in Medicine and Biology*, 1:1–16, 1971.

* cited by examiner

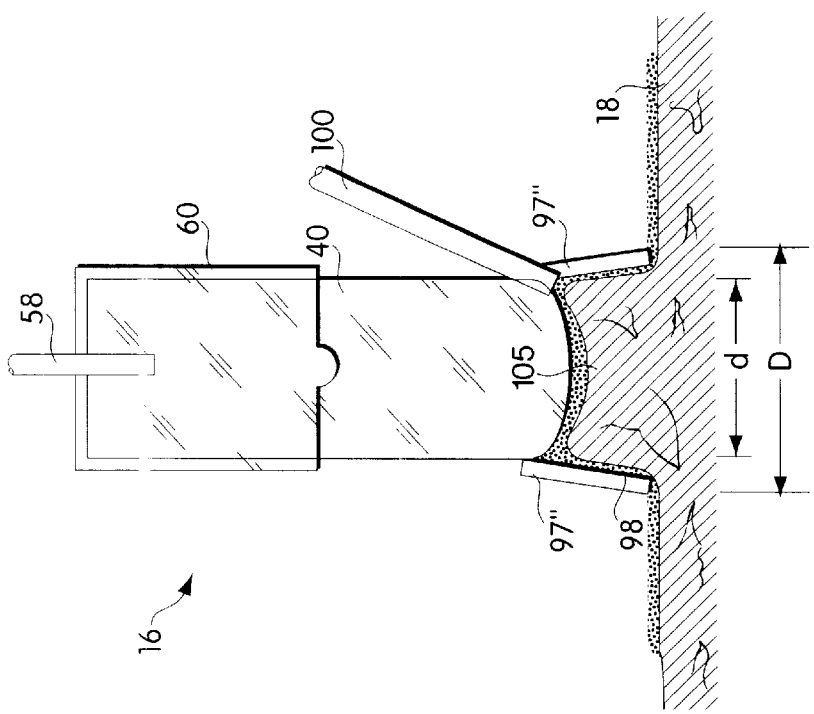
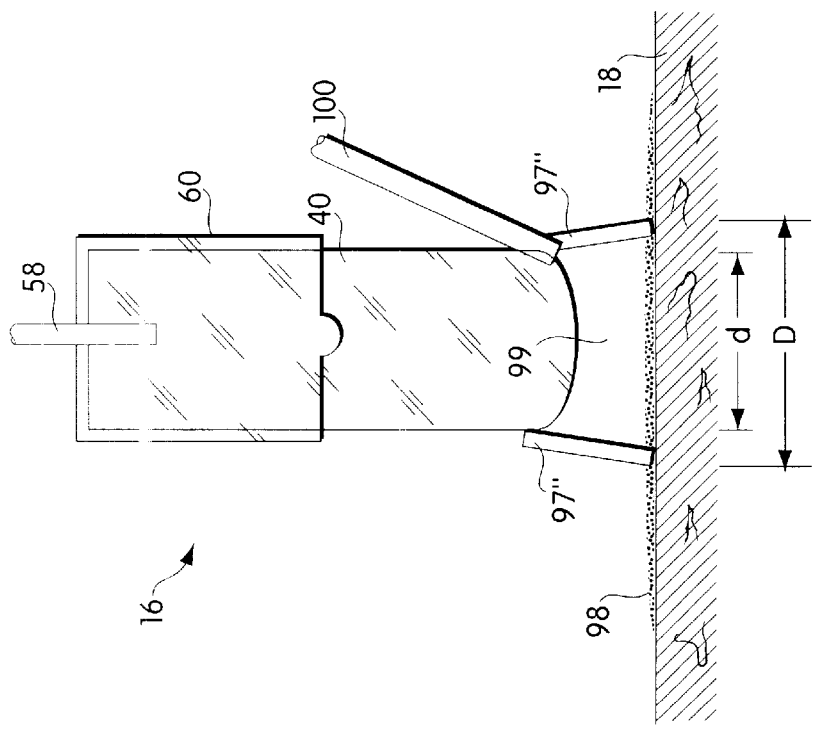

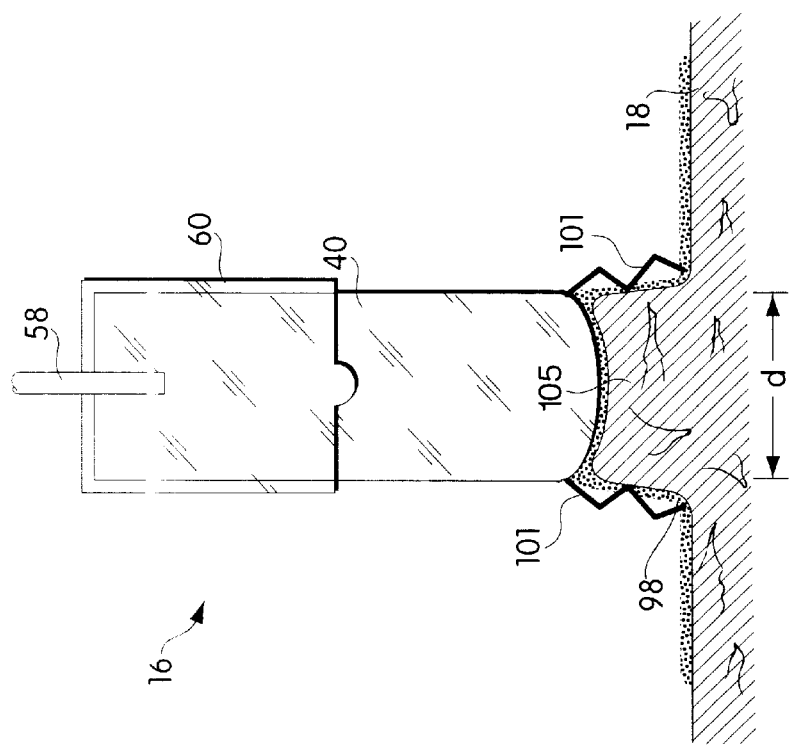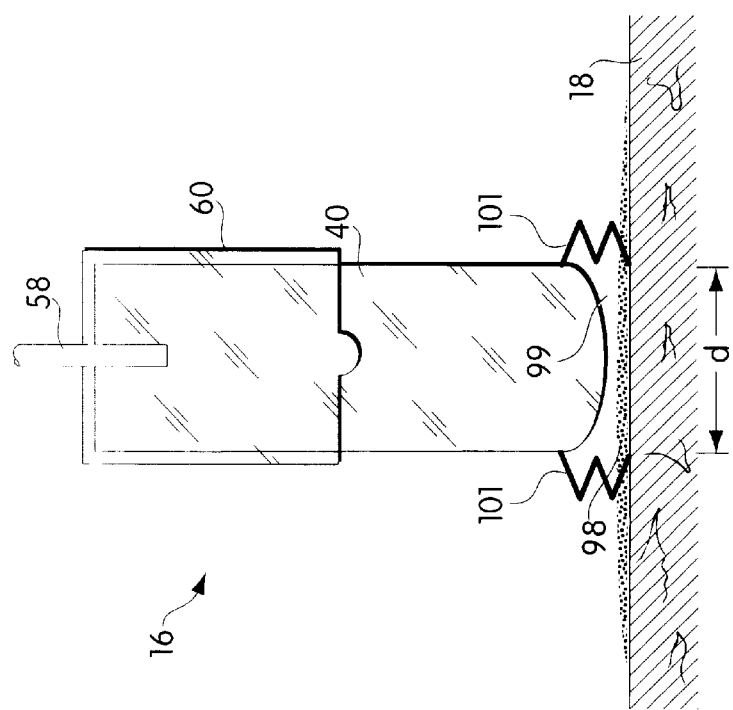

SYSTEM FOR ELECTROMAGNETIC RADIATION DERMATOLOGY AND HEAD FOR USE THEREWITH

RELATED APPLICATIONS

This application is a continuation in part of application Ser. No. 08/759,036, now U.S. Pat. No. 6,015,404 and of application Ser. No. 08/759,136, abandoned both filed Dec. 2, 1996, and now U.S. Pat. No. 6,273,844 of application Ser. No. 09/078,055, filed May 13, 1998 and claims priority of provision application No. 60/077,794 filing date Mar. 12, 1998, and provisional application No. 60/115,447, filed Jan. 8, 1999, which applications are all incorporated herein by reference.

FIELD OF THE INVENTION

This invention relates to the utilization of electromagnetic (EM) radiation for treating selected dermatologic problems, and more particularly to a system which utilizes temperature detection at a waveguide though which radiation is being applied to the patient's skin to perform various control functions and to a head usable in such system or elsewhere, which head includes efficient reflectors for back-scattered radiation and/or for otherwise enhancing irradiation of a target volume containing the dermatologic problem.

BACKGROUND OF THE INVENTION

Lasers, lamps and other sources of electromagnetic radiation are being increasingly utilized to treat various dermatological conditions, and in particular for the removal of unwanted hair, spider veins, leg veins, other veins or blood vessels which are visible through the patient's skin, lesions, port-wine stains, tattoos and the like. One problem with such treatments is that the only way to get the radiation to a target volume in the dermis where treatment is desired is to transmit the radiation to such volume through the overlying epidermis. Further, since many of the treatments involve absorption of energy by melanin in the dermal volume being treated, for example in a hair follicle, and there is also melanin in the epidermis, particularly in the portion thereof at the dermal/epidermal (DE) junction, the EM radiation used for treatment is generally also absorbed to varying degrees in the epidermis. Further, the deeper in the dermis the treatment is desired and/or the larger the element being treated, the more energy must be used, this generally involving use of a more powerful laser or other radiation source with higher fluence and/or operating such source for longer time durations. However, as the energy applied through the epidermis increases, the potential for damage to the epidermis as a result of energy absorption therein also increases.

Therefore, one limitation on the energies which can be used for various dermatological treatments in the dermis, and in particular on the depths in the dermis at which treatment can be performed, and on the size of the elements which can be treated, is that the energy applied cannot be so high as to cause appreciable damage to the epidermis. Various ways around this problem have been proposed in the prior art, most of which involve some cooling of the epidermis prior to and/or during treatment to limit or prevent thermal damage thereto. Examples of such procedures include applying cryogenic or other cooling sprays to the skin, applying a cooling gel to the skin, applying radiation through a cold-pack in contact with the skin or through an applicator which is cooled by flowing water, flowing air, or the like. However, these prior art systems have not been wholly satisfactory. One reason for this is that, since most of the absorption is in the melanin located in the lower portions of the epidermis, it is desirable to have cooling through the entire epidermal layer, which is typically about 0.1 mm thick. However, it is not desirable that the cooling extend significantly below the DE junction into the dermal layer since cooling in the dermal layer can potentially inhibit the desired thermal damage to follicles, blood vessels or the like in this region. Further, there are significant variations in radiation absorption by a patients skin, not only among different individuals, people having darker skin absorbing more radiation and being more prone to epidermal damage than people with lighter skin, but even for different areas on the body of a single individual. Therefore, cooling which is not customized to the treatment area generally results in the cooling not being to the proper depth, a problem which can interfere with treatment and/or permit thermal damage to the epidermis.

It would therefore be desirable if the temperature at a selected depth in the skin, for example the DE junction, could be measured, and this temperature utilized to control skin temperature, for example through the epidermis, by some combination of controlling the laser energy applied to skin and/or controlling cooling applied to the skin. However, while infrared sensors have for example been utilized in the past to detect temperature at the surface of the skin, such detection does not provide an accurate indication of temperature even at the skin surface, these readings varying with such factors as skin layer thickness, skin roughness and skin color in addition to temperature. Infrared sensors also provide virtually no information as to skin temperature at a depth below the surface. Therefore, such detection has heretofore been used only for gross controls, for example to turn off the laser if an emergency temperature threshold is exceeded or the like, but not to fine tune energy application and/or cooling so as to maintain a desired temperature at a selected depth, for example at the DE junction, thereby facilitating a desired treatment without epidermal damage.

A need therefore exists for an improved technique which permits more accurate determinations of skin temperature at various depths, including at the DE junction, so as to permit more accurate and more automatic control of EM radiation treatments for various dermatological conditions. In particular, because of variations in skin pigmentation, differences in epidermal depth, and other dermatological differences among patients, laser dermatology procedures are now performed almost exclusively by physicians or other highly trained individuals, and such individuals must exercise great care to assure that epidermal damage does not occur, while still achieving the desired therapeutic effect. More accurate measurement of temperature at desired depths would make treatments by such skilled personnel easier to perform and would permit such procedures to be safely performed by less highly trained, and therefore less expensive, personnel. Such skin temperature measurements could also be utilized to determine skin type/pigmentation for the patient and/or for the part of a patient's body being treated and/or for other purposes.

Where cooling of the epidermis is achieved by placing a cooled applicator or other cooled body in contact with the patient's skin, the contact must be made with sufficient pressure to assure good thermal contact between the cooled body and the skin. However, differences in skin thickness and elasticity, differences in bone backing and other factors affect the pressure required to achieve good thermal contact for different patients and for different areas on the body for the same patient. This is another reason why highly trained and skilled individuals are required for performing the treatments and contributes to the high cost of the treatment. It would therefore be preferable if an automatic technique could be provided for detecting, and thus assuring, good thermal contact between a cooling element and the patient's skin. Such a technique or mechanism, by assuring good thermal contact with the skin before the radiation source is fired, could solve two critical safety problems for radiation dermatology. First, it assures adequate cooling of the epidermis before heating thereof through energy absorption; and second, it assures that the radiation will not be accidentally applied to the eyes or other unwanted place.

Related but opposite problems arise in performing certain skin resurfacing/wrinkle removal procedures where the objective is to heat and destroy only the most surface layer of the skin, for example the epidermis, with minimal damage to underlying layers. This requires tight control of factors such as laser energy, pulse duration and repetition rate. However, variations in patient's skin make such tight control difficult even for highly trained and skilled personnel. Similar problems also arise in other dermatological procedures involving lasers or other radiation sources.

Another related problem in using an EM radiation source for dermatological treatment is that the skin reflects back a significant portion of the radiation applied thereto. Since this reflected energy does not reach the treatment site, a higher energy radiation source is required to achieve the desired dermatological treatment than would be the case if a larger percentage of the applied radiation reached the treatment site. It has previously been suggested that one solution to this problem is to provide a retro-reflector which collects and returns such back-scattered radiation to the patient's skin. However, existing retro-reflector devices have not optimized the collection and return of such back-scattered radiation and improved techniques for the more efficient reutilization of back-scattered radiation is therefore desirable. One particular problem with prior art retroreflectors is that they reflect all back-scattered radiation at substantially the same angle the radiation was received; however, radiation at an angle more parallel than perpendicular to the skin surface generally does not reach the treatment area and therefore only heats the surface of the skin, contributing to thermal damage of the skin, without having any beneficial/therapeutic effect. A retroreflection technique which does not contribute to or increase this "parallel" radiation would therefore be desirable.

Two other factors can contribute to the efficiency of dermatologic treatments. The first factor is "spot size" or in other words the optical aperture of the applied radiation. Spot size is typically limited by the optics of the handpiece utilized and by the desired fluence as a function of the available energy source. However, a larger spot size permits treatment of large body areas such as back or legs to be accomplished much more quickly, something which enhances both patient satisfaction and practitioner profitability. A technique for facilitating larger spot sizes is thus desirable.

Secondly, anything which reduces the distance from the irradiation source to the target area reduces the amount of energy required to achieve a desired therapeutic effect and anything which permits more of the applied energy to reach the target area has a similar effect. Techniques which facilitate the achievements of these objectives are therefore also desirable.

SUMMARY OF THE INVENTION

In accordance with the above this invention provides both a system for treating a selected dermatologic problem and a head for use in such system. The head, for preferred embodiments includes an optical waveguide or other light path for directing EM radiation of a wavelength appropriate for treating the selected patient dermatologic problem to a first end of the waveguide, the waveguide also having a skin-contacting second end which is opposite the first end; and a sensor at the second end of the waveguide, or otherwise closely adjacent a skin-contacting surface of the head, which senses the temperature thereat. For preferred embodiments, the head also includes a mechanism for removing heat from the waveguide. In order to achieve commercially useful sensitivity, it is preferable that the sensor be located no more than a few millimeters from the skin-contacting surface of the head, for example, the second end of the waveguide, the end contacting the patient's skin. Therefore, for preferred embodiments, the sensor is located within 5 mm of the second end of the waveguide, and for the most preferred embodiments the sensor is located within 1 mm of the second end.

Where a mechanism for removing heat is provided, such mechanism preferably includes a thermoelectric device having one side in thermal contact with the waveguide and an opposite side in thermal contact with a temperature sink. For a preferred embodiment of the invention, back-scattered radiation is substantially internally reflected within the optical waveguide, and there is a reflector within the waveguide for returning back-scattered radiation through the waveguide to the patient's skin. While the reflector may be at a variety of locations within the waveguide, for a preferred embodiment, it is located at the first end of the waveguide. The reflector may also be along sides of the waveguide and the coefficient of reflection for areas of the reflector, either at the first end, the side walls or both, may be selected such that back scattered radiation which, before entering the waveguide, at angles nearer perpendicular to the patient's skin are reflected more strongly than backscattered radiation which, before entering the waveguide, are at angles more nearly parallel to the skin surface. The second end of the waveguide in contact with the patient's skin may also have an aperture which is at least substantially as great as the aperture of radiation back-scattered from the patient's skin or a "reflection aperture" substantially as great as the radiation back-scatter aperture may be achieved in other ways. For example, a reflector plate of size to provide the desired reflection aperture may surround the second end of the waveguide. More generally, the invention may include at least one waveguide passing through the head and terminating at a skin-contacting surface thereof, EM radiation being applied through the at least waveguide path to the patient's skin; and a reflection means for returning back-scattered radiation to the patient's skin, which reflection means has a reflection aperture at least substantially as great as the radiation back-scatter aperture. Reflection means may include at least a portion of the skin-contacting surface of the head, which portion may be in the form of a reflection plate, and may also include at least one reflection surface for back-scattered radiation entering the waveguide, at least part of which surface may be in the waveguide.

The system may be for treating a selected dermatological problem in a selected volume of a patient's skin at a depth d which is below the DE junction. A source of EM radiation of a wavelength appropriate for treating the problem is provided along with an optical waveguide, a mechanism which cools the patient's skin, at least in the portion thereof in contact with the waveguide when the second end of the waveguide is in contact with the patient's skin, and a temperature sensor at the second end of the waveguide. The temperature at the sensor is indicative of the temperature at the patient's DE junction. Finally, controls are provided which are operative in response to the sensor indicating that the DE junction has been cooled to at least a selected temperature for permitting radiation from the source to be passed through the waveguide to the patient's skin. The cooling mechanism preferably removes heat from the waveguide; when in contact with the patient's skin, the waveguide removing heat from and thus cooling the skin. The controls may also be operative in response to the sensor for maintaining the DE junction within a selected temperature range during application of radiation to the patient's skin. The controls may also detect a selected temperature/time profile at the sensor, the profile being indicative of contact of the waveguide with the patient's skin, and may prevent radiation from passing to the patient's skin unless the predetermined profile is detected. This assures that radiation is not applied to the patient's skin unless there is good thermal contact between the radiation-applying waveguide of the head and the patient's skin. For preferred embodiments, the controls operate the cooling mechanism to cool the waveguide to a desired temperature, the controls being responsive to the sensor for determining when the desired temperature has been reached.

The controls may also be operative in response to the sensor sensing a selected increasing temperature profile at the sensor when the waveguide is placed in contact with the patient's skin for permitting radiation from the source to be passed through the waveguide to the patient's skin. This control may be instead of the control based on detection that the DE junction has been cooled to a selected temperature, but is preferably in addition thereto.

The enhanced retro-reflector features discussed above may also be used in the head independent of the temperature measuring features previously discussed, but are preferably used in conjunction therewith. The invention may also include a head having at least one optical waveguide for receiving EM radiation and for directing it to a skin-contacting surface of the at least one waveguide and a standoff having a first and a second end, with the first end surrounding the at least one waveguide at its lower end and forming a substantially air-tight seal therewith. The second end of the standoff is adapted to be in contact with the patient's skin over the selected volume to form a chamber between the skin-contacting waveguide surface, the patient's skin and walls of the standoff. A means is also provided for creating negative pressure in the chamber to draw the patient's skin therein and into contact with the skin-contact surface. The walls of the standoff are preferable reflective to return back-scattered radiation to the patient's skin. The means for creating negative pressure may include a hose mounted at one end to open into the chamber and connected at its other end to a source of negative pressure. Alternatively, the means for creating negative pressure may include the walls of the standoff being deformable when pressure is applied to the head/waveguide to permit the skin-contacting surface of the waveguide to contact the patient's skin, forcing most of the air from the chamber, with the walls of the standoff returning to the their undeformed state when pressure is released, resulting in the creation of negative pressure in the chamber. For example, the walls of the standoff may be in the form of a bellows, suction cup or elastic ring.

Finally, rather than a single optical waveguide, the output surface of a first optical waveguide to which irradiation is initially applied may be mounted to a first surface of a second optical waveguide which also has a second skin-contacting surface opposite the first surface. Optical radiation received from the first waveguide is transmitted through the second waveguide to the skin-contacting surface thereof. The second skin-contacting surface of the second waveguide has a larger area than the output surface of the first waveguide and the second waveguide is formed to provide a larger optical aperture than of the first waveguide. The ratio of the spacing between the first and second surfaces of the second waveguide and a selected surface dimension of the skin-contacting surface of the second waveguide, for example the length of a side of the second surface or a diameter thereof, is approximately 1.5 to 1. Means may be provided for reflecting radiation back-scattered from the patient's skin into the second waveguide back into the patient's skin. The means for reflecting may include forming at least a portion of the first surface and/or other surfaces of the second waveguide so as to reflect radiation impinging thereon, and such reflection from the second waveguide may also be made angle dependent.

The foregoing and other objects, features and advantages of the invention will be apparent from the following more particular description of preferred embodiments of the invention as illustrated in the accompanying drawings.

IN THE DRAWINGS

FIGS. 6a and 6b are simplified side sectional views of a head or applicator which utilizes negative pressure to draw a fold of skin into a cavity before negative pressure is applied and after negative pressure is applied respectively.

FIGS. 7a and 7b are simplified side sectional views of a head or applicator for another embodiment of the invention which utilizes negative pressure to draw a fold of skin into a cavity at an intermediate step in the creation of the negative pressure and after negative pressure has been created respectively.

DETAILED DESCRIPTION

Figure 1:
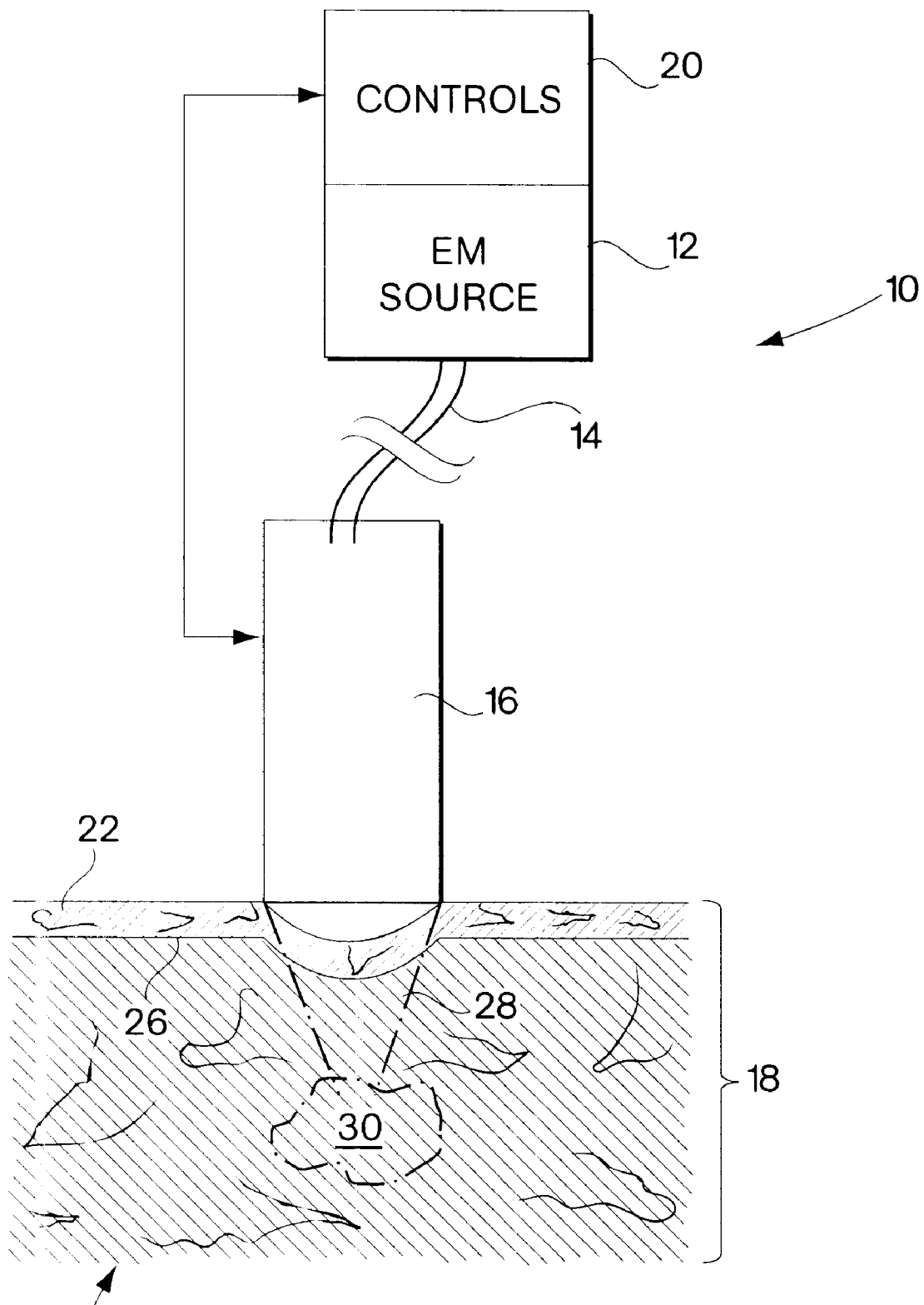
FIG. 1 is a schematic semi-block diagram of a simplified EM radiation treatment system suitable for use in practicing the teachings of this invention.

FIG. 1 is a simplified block diagram of a system 10 which may be utilized for treating a selected dermatological condition in accordance with the teachings of this invention. The system includes an electromagnetic (EM) radiation source 12 which is connected through a fiber optic light pipe or other suitable optical conveyor 14 to an applicator or head 16, which head is in contact with the skin 18 of a patient. Controls 20 are provided which receive information from source 12 and head 16 and which control operation of the system in response to these inputs and others. EM source 12 may be a ruby laser, alexandrite laser, diode laser or other laser source providing radiation of a suitable wavelength for the laser treatment to be performed, or may be a lamp or other non-coherent electromagnetic radiation source providing signals at the requisite wavelength. Particularly for non-coherent light sources, various techniques may be utilized to filter, frequency shift or otherwise control the output from the source to achieve radiation within a desired wavelength band. The radiation wavelength may be narrow band, down to a single wavelength, or wide band, and may vary over a wide spectrum from infrared through ultraviolet, depending on the treatment to be performed and the radiation source utilized. Source 12 may be a pulsed source, either under operator control or at a fixed or controlled repetition rate, or may, as taught in copending applications Ser. No. 09/078,055, be a continuous wave (CW) source. Controls 20 may be a suitably programmed general purpose or special purpose computer, may be hard wired circuitry, or may be a hybrid of special purpose circuitry and programmed computer circuitry. Skin 18 has an epidermal layer 22, and a dermal layer 24, the junction of these two layers being sometimes referred to as the DE junction or basal layer 26.

Radiation from source 12 passes through head 16 and is emitted therefrom as a converging beam 28 which is applied to an area 30 in dermis 24 containing the element to be treated. Area 30 may, for example, contain a hair follicle which is to be destroyed in order to achieve removal of unwanted hair, may be tattoo pigment which is to be removed, may be a spider vein or other blood vessel which is to be coagulated and removed or may be some other dermatological condition which is to be treated by the radiation. As discussed earlier, treatment of a patient is complicated by the fact that there may be significant variations among patients, and in different areas of the body of the same patient, in the thickness of epidermal layer 22, in the pigmentation of this layer (and in particular in the quantity of melanin at DE junction 26), and in other characteristics of the skin. These variations make it difficult to achieve a desired therapeutic effect without potential damage to the area of the patient's epidermis overlying treatment area 30.

Figure 2:
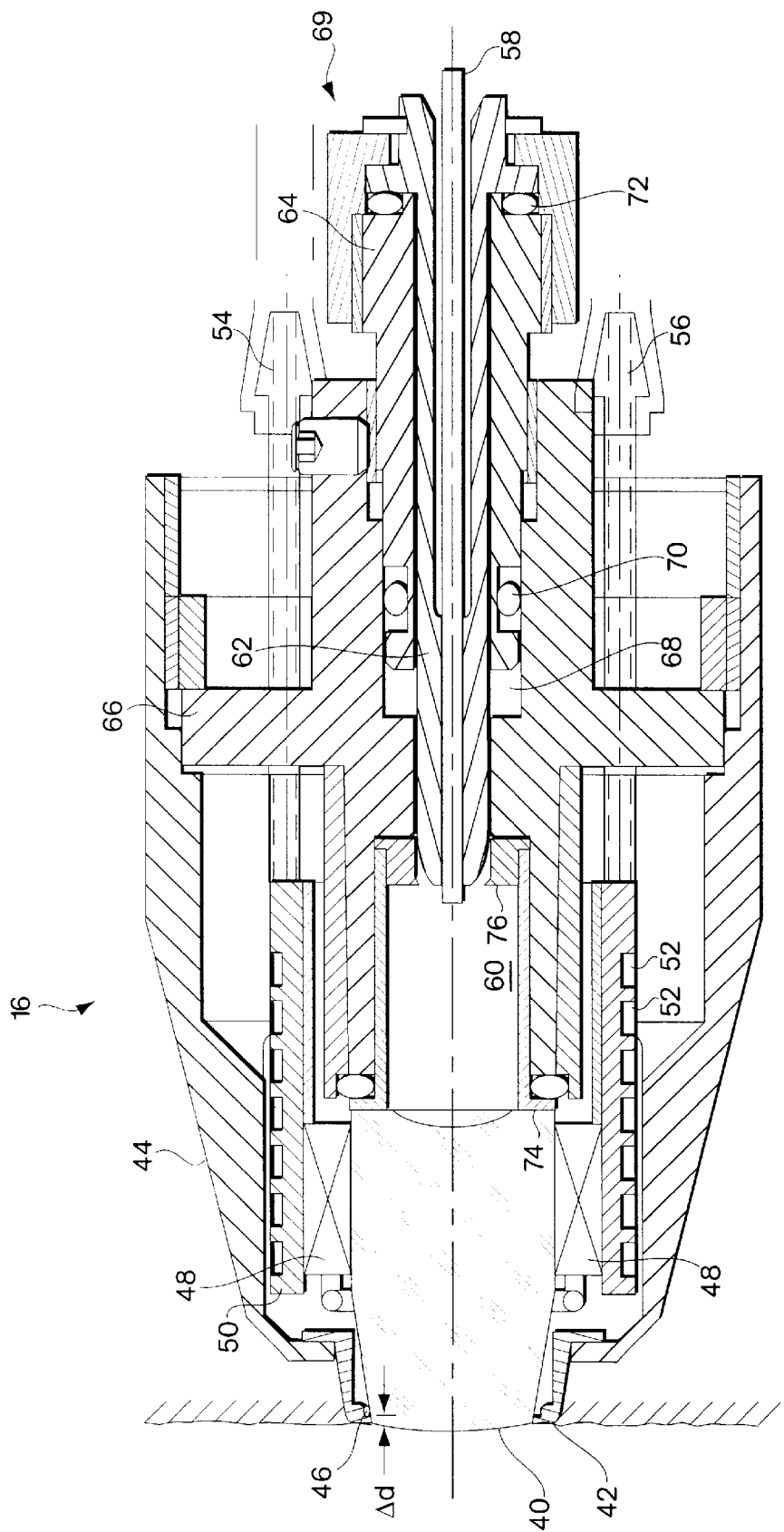
FIG. 2 is a side sectional view of a head or applicator suitable for use in the system of FIG. 1 in accordance with teachings of this invention.

FIG. 2 illustrates a head 16 suitable for use in the system of FIG. 1. Referring to FIG. 2, head 16 includes a waveguide or lens 40 of an optically transparent material which also has good heat transfer properties and preferably provides a good index of refraction match with skin. Sapphire is a currently preferred material for the waveguide, although other materials could also be used. Waveguide 40 is supported by a holder ring 42 mounted in an exterior housing 44. A thermocouple, thermistor or other suitable temperature sensor 46 is mounted in contact with waveguide 40, between the waveguide and holder 42. The distance ($\Delta d$) of sensor 46 from the end of waveguide 40 in contact with the patient's skin is critical and, for reasons to be discussed later, should be no more than 5 mm. $\Delta d$ is preferably in the 1–2 mm range, with approximately 1 mm being the currently preferred distance. While a single temperature sensor 46 is shown in FIG. 2, two or more such sensors spaced around waveguide 40 at the same distance $\Delta d$ from the end of the waveguide may be preferable to average out temperature variations which may occur in the waveguide.

Thermoelectric cooling elements 48 are also provided in contact with waveguide 40. While two such elements are shown in FIG. 2, typically at least four such elements, substantially evenly spaced around the periphery of waveguide 40, would normally be provided. Thermoelectric elements 48 may for example be Peltier elements. Electrical connections are made to sensor(s) 46 and to thermoelectric elements 48 in a manner known in the art and to simplify the figure are not specifically shown therein.

The sides of thermoelectric elements 48 opposite those in contact with waveguide 40 are in thermal contact with heat sink or radiator 50 having channels 52 formed therein through which a cooling fluid such as air or water flows, the cooling fluid entering the head through a fluid junction 54 and exiting through a fluid junction 56 (or entering though fluid junction 56 and exiting through fluid junction 54).

Optical radiation is applied to the head through an optical fiber, fiber bundle or other light pipe 58 which terminates at a chamber 60. Radiation exiting optical fiber 58 expands in chamber 60 before entering waveguide 40 for application to the patient's skin. Fiber 58 is mounted in a sleeve 62 of optically opaque material, the rear portion of which is mounted in a tube 64 and the forward portion of which extends through a holder assembly 66. Tube 64 is mounted in a chamber 68 formed in the rear of holder assembly 66 to permit assembly 69, which includes fiber 58, sleeve 62 and tube 64, to be moved forward and backward, moving fiber 58 in chamber 60 to adjust the optical aperture of the head. O-rings 70 and 72 seal chamber 60 to keep air and moisture out so as to avoid condensation on cooled optical surfaces 74 and 76. Nitrogen or another gas which does not condense at temperatures down to −40° C. is utilized to fill chamber 60.

Surface 74 of the waveguide is an optical reflecting surface as are all surfaces of chamber 60, including surface 76 at the rear thereof. As will be discussed later, these surfaces retroreflect back-scattered light from the patient's skin. The side walls of both waveguide 40 and chamber 60 may also be fully reflective or may selectively reflect in a manner and for reasons to be discussed later.

In operation, assembly 69 is initially positioned to achieve a desired optical aperture for head 16. Thermoelectric elements 48 are also energized to cool waveguide 40 to a selected temperature, for example 10° C. to −40° C. The criteria is to bring the waveguide 40 to a sufficiently low temperature to achieve the desired cooling of epidermis 22 without resulting in tissue temperature being brought down to a level where water in the cells might freeze. Good results have been achieved with a waveguide temperature in the 0° C. to −30° C. range, with a preferred temperature of approximately −10° C.

When the above preliminary steps have been completed, head 16 may be brought into physical contact with an area of the patient's skin where treatment, is to be performed. This contact may be under low pressure, preferably at least sufficient to establish good thermal contact between waveguide 40 and the patient's skin, where the objective is to coagulate blood in for example a spider vein, leg vein or other vein or blood vessel, or may be under pressure greater than the patient's blood pressure for hair removal or other applications where it is preferable to remove blood from the region of skin between waveguide 40 and area 30 under treatment.

Figure 3A:
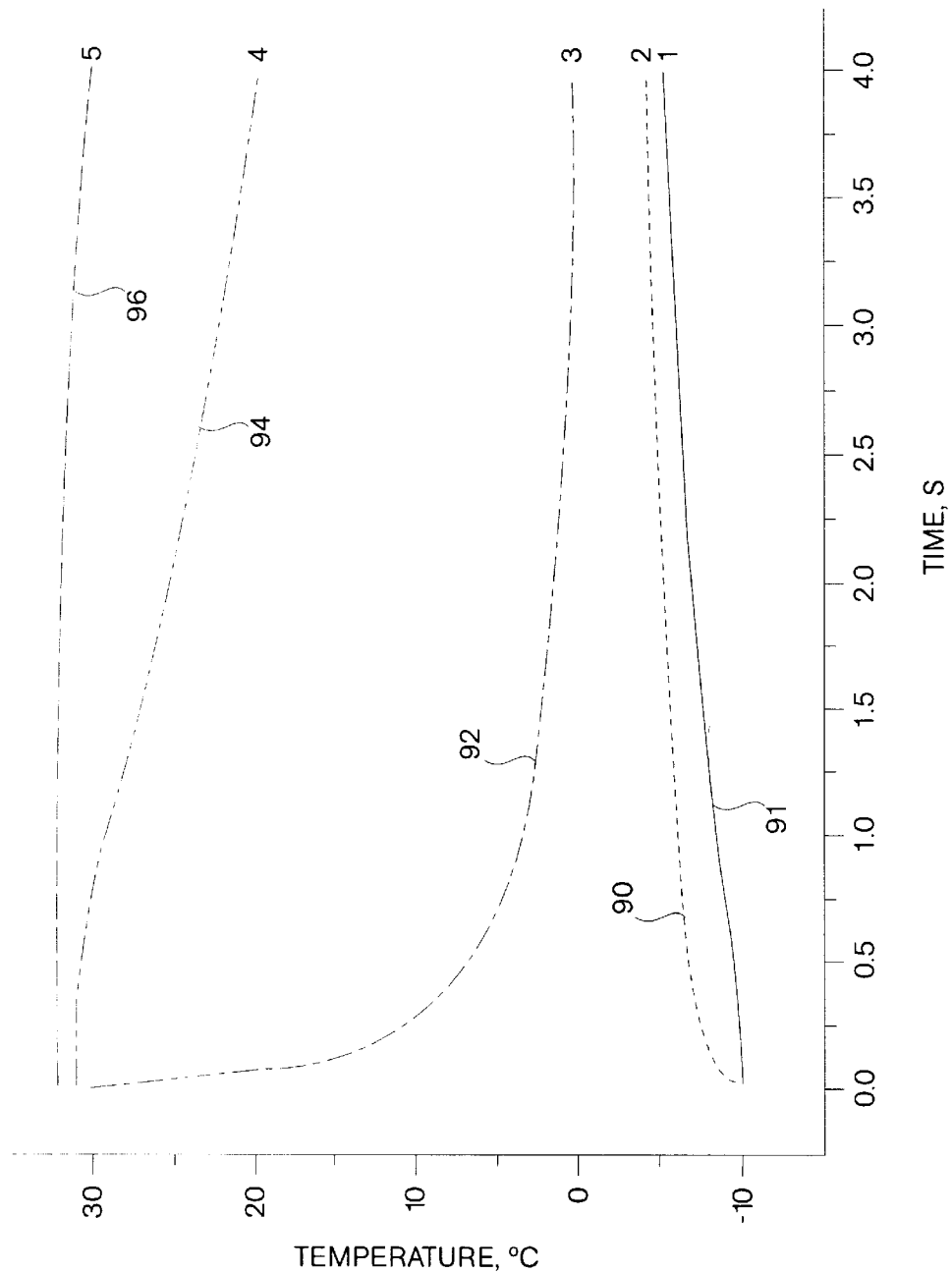
FIG. 3a is a graph illustrating a calculated relationship over time between the temperature at the waveguide at two Δd's where a sensor may be located and the temperature at three different depths in a patient's skin, including at the DE or basal junction.
Figure 3B:
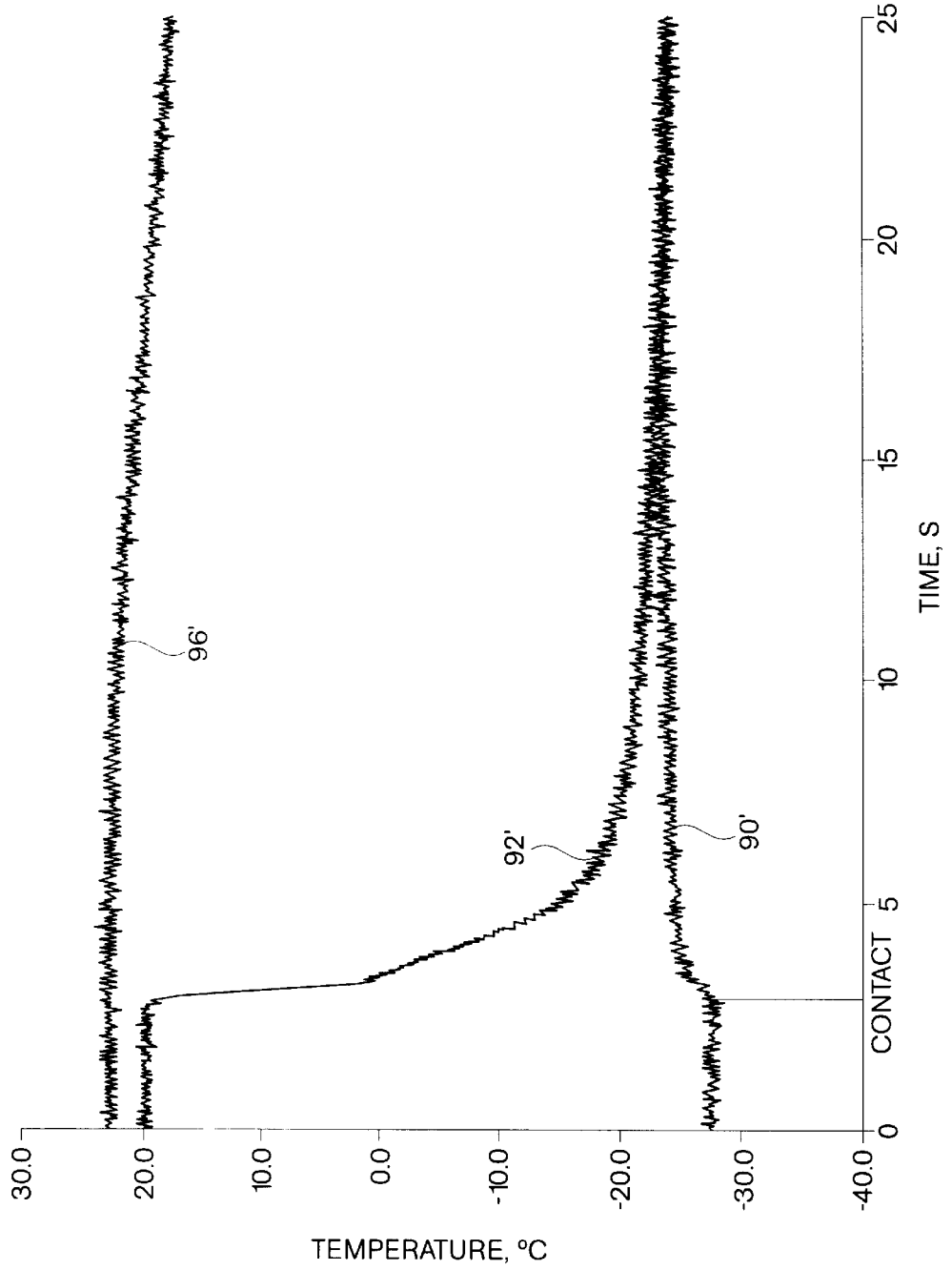
FIG. 3b is a graph illustrating a measured relationship over time between the temperature at the waveguide sensor for a preferred Δd and the temperature at two different depths in a patient's skin, including at the DE or basal junction.

In any event, head 16, and in particular waveguide 40 thereof, should be placed in contact with the patient's skin with sufficient pressure to assure good thermal contact between the patient's skin and waveguide 40. In accordance with the teachings of this invention, the fact that such good thermal contact has been established can be detected through use of sensor 46. In particular, as seen in FIGS. 3a and 3b, with the sensor positioned approximately 1 mm from the contact surface of waveguide 40, (i.e. $\Delta d=1$ mm), the temperature at the sensor has a profile 90 in FIG. 3a and 90' in FIG. 3b which increases sharply for the first quarter to one-half second after such thermal contact has been established. The reason for this is that the waveguide is acting as a heat sink for the patient's skin during this time interval and the heating of the waveguide at the skin-contacting end thereof is greater than the cooling effect of thermoelectric device 48 at this surface (i.e. there is a small temperature gradient across waveguide 40). The detection of the temperature profile 90, 90' by sensor(s) 46 can be interpreted by controls 20 as an indication of good thermal contact between the waveguide and the patient's skin. If such a thermal profile is not detected, controls 20 inhibit the activation of radiation source 12 and/or prevent radiation from the source being applied to head 16. This assures that radiation is not delivered to the skin unless the epidermis has been adequately cooled to prevent thermal damage thereto.

Referring for example to FIG. 3a, it is seen that the placement of sensor 46 relative to the skin-contacting surface of waveguide 40, or in other words the distance $\Delta d$, is critical in order to achieve this objective. In particular, while profile 90 is achieved for a $\Delta d$ of approximately 1.2 mm, profile 91, which is achieved with a $\Delta d$ of approximately 4.8 mm, evidences far less sensitivity to temperature changes at the DE junction and is therefore not particularly useful in assuring good thermal contact between the waveguide and the patient's skin. Actual profile 90' (FIG. 3b), while slightly more stepped and less smooth than the theoretical profile 90 of FIG. 3a, is sufficiently similar to this profile so as to permit easy identification of good thermal contact. Differences between FIGS. 3a and 3b may also arise from the fact that the waveguide in FIG. 3a starts at a temperature of $-10°$ C. while the waveguide in FIG. 3b starts at a temperature of approximately $-27°$ C.

Referring again to the Figures, and in particular to FIG. 3a, it is seen that a major portion of the waveguide cooling occurs within a period of between 0.5 and 2 seconds from full contact, the time varying somewhat with the initial temperature of the waveguide and the desired final temperature at the DE junction. Therefore, assuming good thermal contact has been made, an operator may operate source 12 some predetermined time after making contact with the patient's skin, for example a half second thereafter, but not more than approximately 2 seconds thereafter, to avoid significant cooling of the dermis.

However, since cooling of the skin may vary depending on a number of factors, including variations in the equipment being utilized, the color and nature of the patient's skin, the thickness of the patient's skin and the like, it is preferable that the temperature at the DE junction be measured and that the radiation source 12 be operated as soon as this temperature has dropped to a desired level. As can be seen from FIGS. 3a and 3b, the temperature profile 90 at sensor 46 tracks the temperature profile 92 at the DE junction as does the temperature profile 90' for DE junction temperature profile 92'. Thus, the output from sensor 46 can be utilized by control 20 as an indication of temperature at the DE junction, and radiation source 12 can be operated by control 20 when this temperature reaches a predetermined value. This assures that radiation is not applied to the patient until the patient's epidermis has been fully cooled to the desired level and that the operation of laser source 12 is not delayed so long as to cause cooling of portions of the follicle which are to be destroyed. In particular, 94 is a profile taken approximately 1 mm from the surface of the patient's skin, which is approximately the depth of the bulge in a hair follicle, and may be a depth where other dermatological treatments such as tattoo removal, treatment of port wine stain or vascular legions may occur. From FIG. 3a it is seen that for a time over two seconds, there is a significant drop in temperature at this depth, which can be $10°$ C. or more. For many dermatological applications, such a drop in temperature 1 mm into the dermis is undesirable, and in particular can adversely affect the desired treatment. Curves 96, 96' are temperature profiles with time deeper into the dermis, for example 2 mm therein. At this depth, the cooling effect of cooled waveguide 40 is not significant, perhaps a few degrees Celsius. This lack of cooling effect at deeper depths stems both from the greater distance of these point from the cooling source and from the proximity of tissue at this depth to the warming effect of blood-carrying vessels. The teachings of this invention thus permit and assure that the radiation source is not operated to cause heating of the patient's epidermis until the epidermis has been cooled to the desired depth and temperature, but that firing of the radiation source occurs before there is any significant cooling of the dermis. The invention further permits these controls to be performed completely automatically, thereby reducing the skill level required to safely perform such dermatological procedures, and permitting such procedures to be performed by less skilled and therefore less expensive personnel.

During the firing of the radiation source, control 20 continues to monitor the temperature at sensor 46. If at any time during the firing of the radiation source, there is an increase in temperature at sensor 46 which deviates from what would be anticipated from profile 90, controls 20 can immediately turn off the source 12 to prevent any thermal damage to the patient's epidermis 22.

While for certain treatments, the system of this invention may be able to detect successful completion of the treatment, this is not easy to do, particularly for treatments being performed several millimeters into the dermis. The radiation source is therefore typically fired for a predetermined time interval and/or head 16 is maintained in contact with the patient's skin for a predetermined time interval. Control 20 may determine when such time interval has expired, turn off source 12 when such time period has passed and perhaps generate an audio or visual indication to the operator to remove head 16 from the patient's skin. These steps also reduce the skill level required for using the system.

As indicated earlier, one problem with utilizing radiation to treat dermatological conditions is that a significant portion of the radiation applied to the patient's skin is back-scattered and lost, therefore increasing the power required from the radiation source utilized, and thus the cost of the system. One solution to this problem is to efficiently collect radiation back-scattered from the patient's skin and to reflect such radiation back into the patient's skin with minimum loss. FIG. 2 shows a retroreflector which is particularly well suited for performing this function. In particular, waveguide 40 has an aperture which is larger than the optical aperture of the radiation applied to the patient's skin and which is instead substantially equal to the aperture of radiation back-scattered from the patient's skin. Thus, substantially all of the back-scattered radiation is collected in waveguide 40. Waveguide 40 has an external coating or is otherwise designed in manners know in the art so as to totally internally reflect the back-scattered radiation collected therein. Some of such radiation impinges on reflecting surface 74 and is returned through the totally internally reflecting waveguide from such surface to the patient's skin. The remainder of the back-scattered radiation extends into chamber 60 which is also totally internally reflected and ultimately impinges on reflecting surface 76 which returns this radiation with minimal loss to the patient's skin. Thus, the retroreflective design for the head 16 in FIG. 2 results in the collection and retroreflection back into the skin of substantially all back-scattered radiation.

In the discussion above, the side walls and back walls of both waveguide 40 and chamber 60 are fully reflecting so that substantially all of the light retroreflected into waveguide 40 is returned to the patient's skin. However, since radiation entering the waveguide from the skin (before refraction on entering the waveguide), is retroreflected back into the patient's skin at substantially the same angle, such radiation at relatively sharp angles, (i.e., at angles more nearly parallel to the patient's skin than perpendicular) contributes primarily to heating the patient's epidermis, potentially causing thermal damage thereto, without reaching region 30, and therefore without having any therapeutic effect. It is therefore preferable that such sharply angled radiation not be retroreflected or that, as a minimum, the retroreflection of such radiation be substantially attenuated. This can be accomplished in the embodiment of FIG. 2 by for example utilizing an angle dependent coating for the side walls of waveguide 40, the rear wall of waveguide 40, or both so that these walls of the waveguide either do not reflect or minimally reflect large angle radiation entering the waveguide, while more strongly reflecting radiation coming in at a more closely perpendicular angle. Alternatively, the side wall may have varying coefficients of reflection, being less reflective for the portions of the wall closest to the tip or skin contacting surface of waveguide 40 and more reflective toward the rear of the waveguide. Other techniques could also be utilized to assure that waveguide 40 and chamber 60 more strongly reflect retroreflected radiation applied thereto at an angle more nearly perpendicular to the skin surface than radiation applied thereto at an angle more nearly parallel to the skin surface, the perpendicular radiation being substantially fully retroreflected, while the parallel radiation is substantially attenuated.

Figure 4:
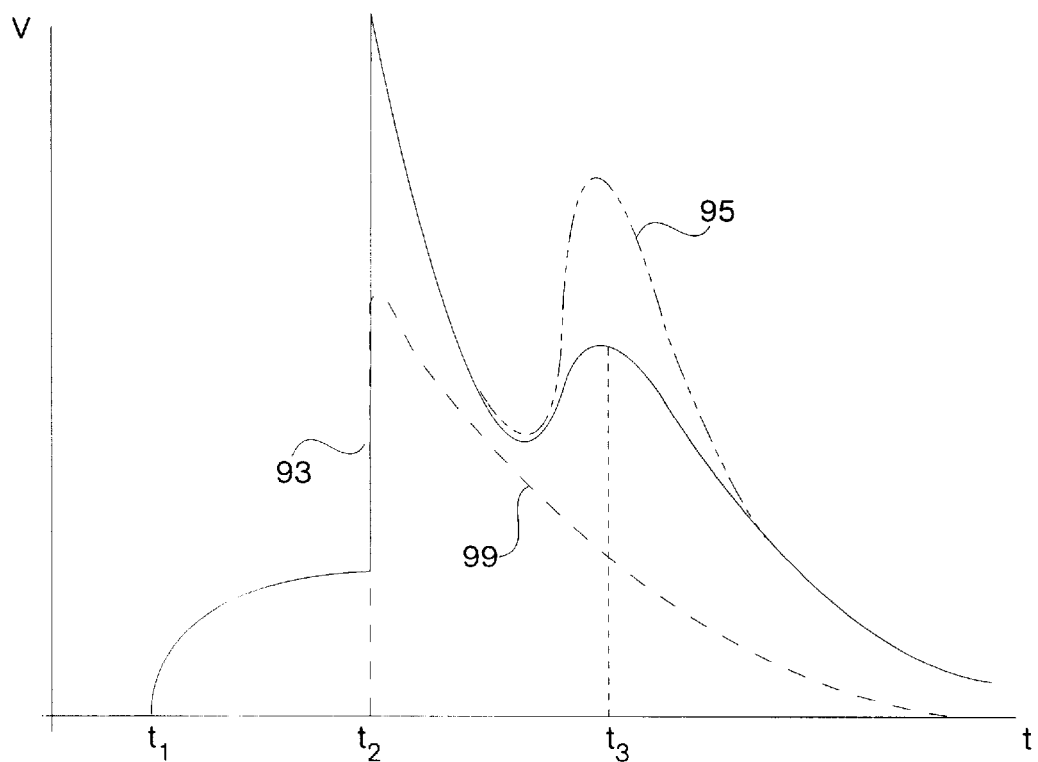
FIG. 4 is a graph illustrating temperature sensor output over time for selected conditions.

FIG. 4 illustrates the voltage output at sensor 46 as a function of time under selected operating conditions. The solid line 93 illustrates a representative output when the waveguide 40 of head 16 is placed in contact with a patient's skin at time $t_1$. From time $t_1$ to time $t_2$ the temperature at the sensor increases as the skin in contact with waveguide 40 is cooled. At time $t_2$, source 12 is operating to apply a radiation pulse through the waveguide to the patient's skin causing an increase in the temperature of the patient's skin which is reflected as a spike in the voltage output from the temperature sensor 46. The temperature then decreases rapidly until just before a time $t_3$ when backskattered radiation from the patient's skin starts to be received in the waveguide. The time between $t_2$ and $t_3$ is a function of the thickness of the patient's epidermis to the DE junction where melanin is being heated and the amplitude of the spike at time $t_3$ is a function the patient's skin type, more energy being reflected for a patient having darker skin, for example spike 95, than for patients having lighter skin. Thus, the amplitude of the spike which occurs at time $t_3$ may be utilized as an indication of the patient's skin type, and this information may be reviewed at least periodically by the system controls, since skin type will vary even for a given patient as different areas of the patient's skin are being treated.

Patient's skin type may also be determined by taking two successive readings, one with head 16 not in contact with the patient's skin and a second with the head in contact with the patient's skin. Curve 93 is an example of the output which is obtained when the head is in contact with the patient's skin, while curve 97 which would start at time $t_2$, is indicative of an output which would be obtained when the laser is fired at time $t_2$ with the head not in contact with the patient's skin. Since the output in air is proportional to the coefficient of absorption for air times the applied laser energy ($V_A = k_0 E$) and $V_s$ when the head is in contact with the patient's skin is given by $$V_s = k_0 E + k_0 RE$$

where R is the coefficient of reflection from the patient's skin, $R = (V_s - V_a)/k_0 E$). Since $k_0$ and E are known values, the difference in voltage for the two readings provides a reliable indication of the coefficient of reflection from the patient's skin in the area under treatment, or in other words of the patient's skin type. The output from temperature sensor 46 may also be utilized for other purposes.

Figure 5A:
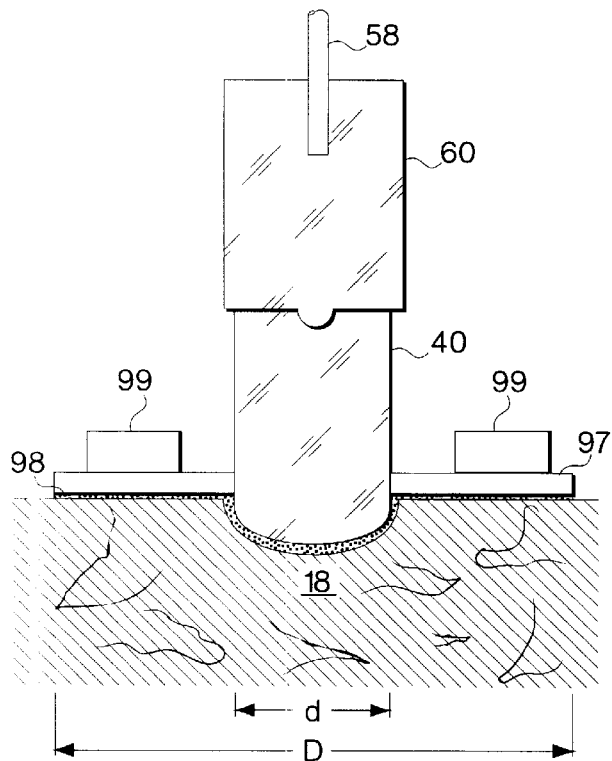
FIGS. 5a and 5b are simplified side sectional views of two alternative heads or applicators for providing a reflection aperture matching the aperture of radiation back-scatter.

FIG. 5a shows an alternative embodiment of the invention for performing the retroreflector function where the surface area or aperture of waveguide 40 is substantially equal to the optical aperture of radiation applied to the patient's skin. It is therefore smaller than the aperture D of radiation back-scattered from the patient's skin. Therefore, a reflector plate 97 is provided, which may be a specular or diffuse reflector. Plate 97 has a hole which is sized and shaped to permit waveguide 40 to fit therein. Plate 97 may, for example, extend for approximately 1 to 6 millimeters on either side of waveguide 40, but this dimension will vary with application, and can be outside the above range for selected applications. The reflective effect can be enhanced by providing a liquid or other reflective index-matching substance 98 between the skin 18 and the waveguide 40/plate 97, which substance has a reflective index equal or greater than the reflective index of the skin. This decreases the total internal reflection from the skin surface, allowing better return of radiation into the deep layers of skin by reflector 97. Thermoelectric elements 99 in contact with reflective plate 97, which may be formed of a material having good thermal conducting properties such as metal, can be utilized to heat plate 97 to a temperature of, for example, 45–50° C. Plate 97 can thus preheat the area of the patient's skin surrounding the area where radiation is to be applied, thereby increasing the temperature at the treatment area in the dermis, and thus decreasing the light energy required for performing the desired treatment.

Figure 5B:
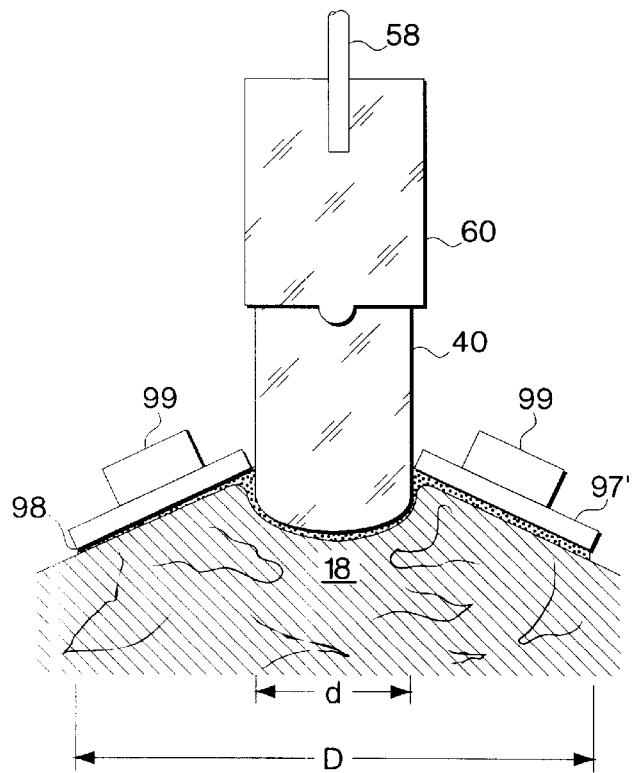

FIG. 5b illustrates an alternative embodiment wherein the reflector 97' has an enhanced efficiency by being formed in a cone or other concave shape. This results in the back-scattered light reflected into the skin being concentrated in the region of the radiation or collimated beam delivered into the skin through waveguide 40, thus increasing the quantity of radiation delivered to the treatment area. Except for the shape of the reflection plate 97', the embodiment of FIG. 5b otherwise functions in the same way as the embodiment of FIG. 5a. As for the embodiment of FIG. 2, retroreflection from waveguide 40 can be angle dependent for the embodiments of FIGS. 5a and 5b and, particularly for the embodiment of FIG. 5a, reflection from plate 97 can also be made angle dependent by suitably coating the reflecting surface thereof.

FIGS. 6a and 6b show another embodiment of the invention which differs from those previously described in that reflection plate 97" is even more angled than for the embodiment of FIG. 5 and is generally in the form of a truncated cone which is secured to the lower end of waveguide 40 in a manner so as to form a substantially air-tight seal therewith. Such securing may be by providing a pressure fit between plate 97" and waveguide 40, but is preferably achieved by applying a suitable adhesive between the two components. Another alternative would be to have some form of screw thread formed in or on waveguide 40 which mates with a corresponding tread on plate 97", but such tread might interfere with the optical properties of waveguide 40. A hose 100 passes between plate 97" and waveguide 40 and is sealed therebetween, hose 100 being attached to a source of negative pressure (for example vacuum pressure) (not shown). As may be best seen in FIG. 6a, when head 16 of this embodiment is pressed against skin 16, a chamber 99 is formed which is defined by the light reflecting walls of plate 97", the lower surface of waveguide 40, and the surface of the patient's skin 18 which is inside the cone of plate 97". Plate 97" will sometimes also be referred to hereinafter as a standoff.

In operation, once head 16 is in the position shown in FIG. 6a, vacuum is applied through hose 100 to chamber 99 to remove air therefrom. This has the effect of drawing a portion or fold 105 of the patient's skin into chamber 99 and into contact with the lower skin-contacting surface of waveguide 40. This can reduce the distance between waveguide 40 and the target volume in skin portion 105 at which treatment is desired and also brings this target volume into chamber 60 where back-scattered radiation retroreflected from the reflecting walls of plate 97" concentrate this radiation on the target volume. This reduces the amount of energy required from EM source 12 and significantly enhances the overall efficiency of the system. The depth of chamber 99 from the bottom of waveguide 40 to the skin surface would typically be in the 5 mm range and should normally not be more than approximately 10 mm. The diameter D of standoff or plate 97" at the skin-contacting end thereof is, as for the embodiment of FIGS. 5a and 5b substantially equal to the aperture of back-scatter radiation.

FIG. 7 shows and embodiment of the invention which differs from that shown in FIG. 6 in that, instead of a vacuum line 100 being utilized to obtain reduced or vacuum pressure in chamber 99, standoff 101 is in the form of a bellows which collapses when head 16 is pressed against the skin as shown in FIG. 7a forcing air out of chamber 99. When pressure on head 16 is removed, or if slight upward pressure is applied to the head, bellows 101 straightens as shown in FIG. 7b. The vacuum in chamber 99 holds bellows 101 against the skin resulting in skin fold 105 again being drawn into chamber 99 as bellows 101 returns to its normal position. The embodiment of FIG. 7 functions substantially the same as the embodiment of FIG. 6 with the inside of bellows 101 having a reflective coating or otherwise being reflective. While the base of bellows or standoff 101 has only a slightly larger aperture than the aperture d of waveguide 40, this is not a problem since substantially all of the back-scattered radiation from the skin is emitted into chamber 99 where it is reflected in a concentrated manner back to the target volume and there should be virtually no back-scattered radiation outside of chamber 99. Sharply angled radiation is also productively utilized for these embodiments. An effect substantially the same as that of FIG. 7 can be achieved by using a standoff in the form of a suction cup in lieu of the standoff's 97" or 101 as shown.

Figure 8C:
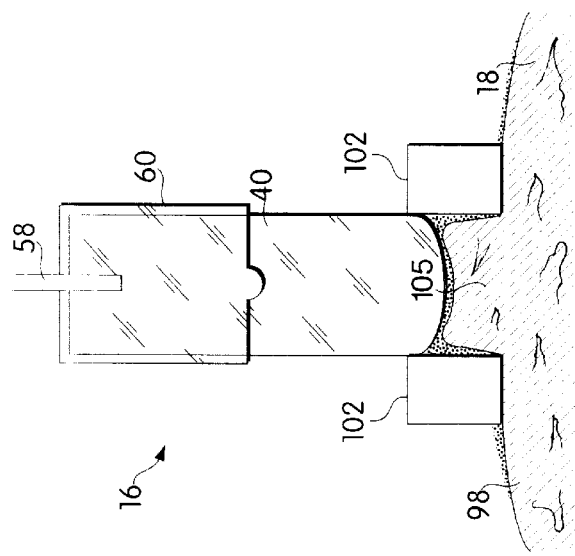
FIGS. 8a, 8b and 8c are simplified side sectional views of a head or applicator for still another embodiment which uses negative pressure to draw a fold of skin into a chamber shown before negative pressure is created, at an intermediate stage in the creation of negative pressure and after negative pressure has been created respectively.
Figure 8B:
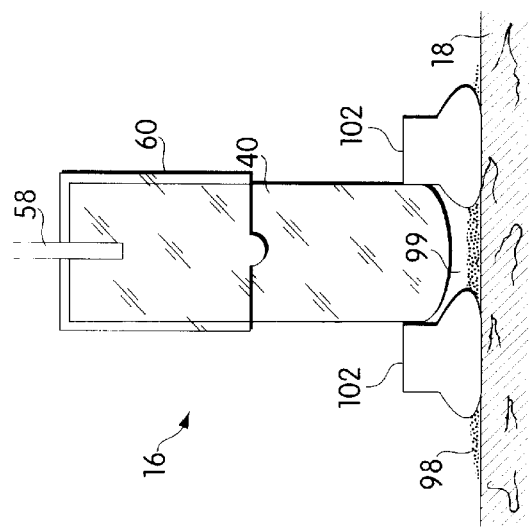
Figure 8A:
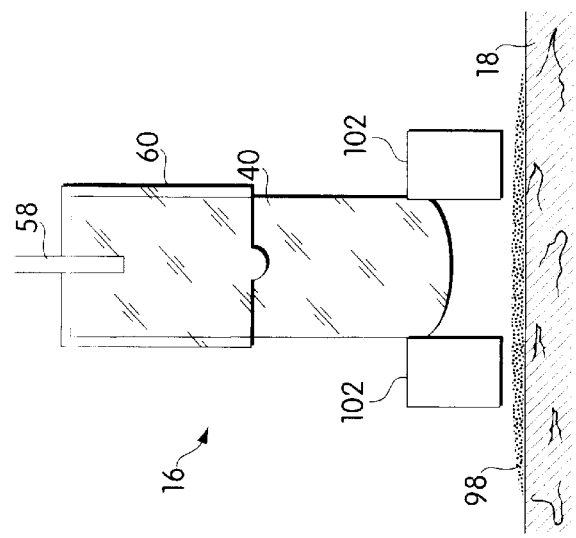

FIGS. 8a–8c shows still another embodiment of the invention which differs from that shown in FIG. 7 in that a ring 102 of an elastic material is substituted for the bellows 101. When ring 102 is pressed against the skin as shown in FIG. 8b, the ring deforms permitting waveguide 40 to move substantially into contact with skin 18 as air is forced out of chamber 99. When the pressure is released, elastic ring 102 returns to the condition shown in FIG. 8c, resulting in skin fold 105 being drawn into the chamber as shown.

While three standoff configurations have been shown and/or described above for achieving vacuum pressure, or at least negative pressure, in chamber 99 by collapsing a standoff and then permitting it to return to its normal position, the embodiments shown and/or described are by way of illustration only, and other standoff configurations for achieving the same objective might also be utilized. Further, in addition to the use of vacuum hose 100 as shown in FIG. 6, other methods known in the art may be used for achieving the desired reduced pressure in chambers 99 so as to cause a fold of skin 105 to be drawn therein for irradiation.

Figure 9:
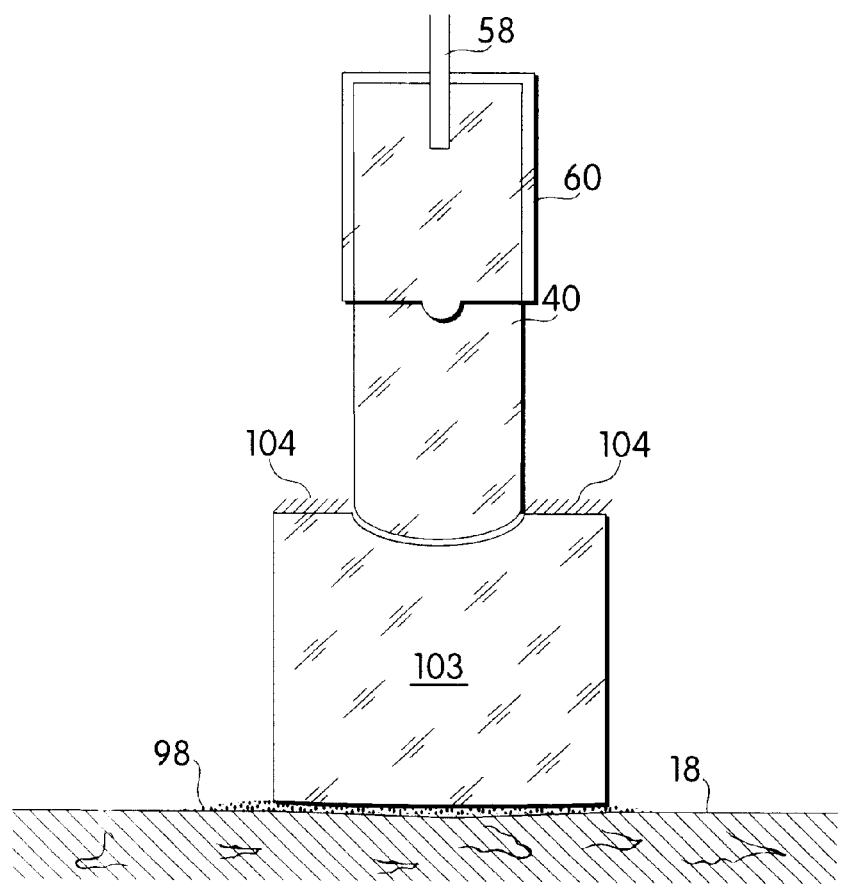
FIG. 9 is a simplified side sectional view of a head for an alternative embodiment of the invention which provides an expanded optical aperture for the head.

FIG. 9 shows still another embodiment of the invention which differs from those previously shown in that, rather than a bottom surface of waveguide 40 being in contact with the patient's skin 18, the lower end of waveguide 40 is in contact with a second waveguide 103 which is preferably of sapphire or other material having good optical and thermal conduction properties. Sapphire is particularly preferred, because it also provides a fairly good optical index match with skin. Index matching material 98 may be utilized between waveguide 103 and the patient's skin to further enhance this match. While not specifically shown in FIG. 9, waveguide 103 would also have, for preferred embodiments, one or more temperature sensors 46 positioned close to its skin-contacting surface and one or more thermoelectric elements 48 or other temperature control elements in contact therewith to preheat and/or cool the patient's skin 18 as required. A reflective coating 104 may also be provided on the rear surface of waveguide 103 to, in conjunction with the retroreflector previously described for waveguide 40, retroreflect substantially all radiation back-scattered from the patient's skin. Angle dependent retroreflection might also be employed for this embodiment using techniques previously discussed, such angle dependent retroreflection occurring at least for waveguide 103, and preferably for both waveguides. The advantage of the embodiment shown in FIG. 9 is that it significantly enlarges the optical aperture for treatment, permitting treatment over a relatively large area, for example hair removal over a patient's legs or back, to be accomplished far more rapidly then when a head having a smaller aperture is utilized. The skin-contacting surface of waveguide 103 may have a variety of shapes, and may for example be circular or square. A circular waveguide 103 might for example have a diameter of approximately 1 inch while a square waveguide 103 might have sides 2 cm long, the height of waveguide 103 preferable being roughly 1.5 times this dimension. These dimensions are, however, being provided by way of illustration only and the specific dimensions of waveguide 103 will vary with application.

Figure 10:
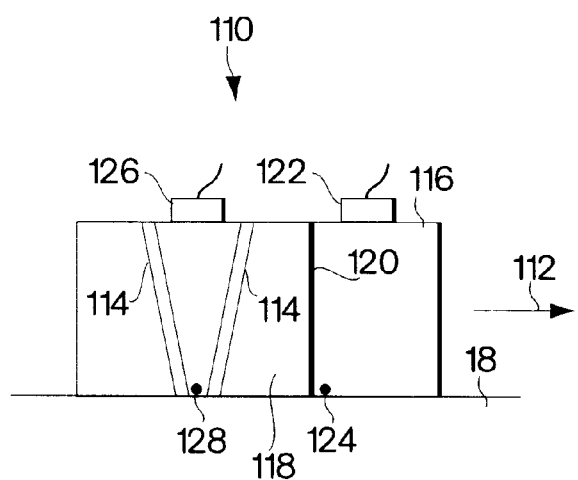
FIG. 10 is a simplified side sectional view of a head for an alternative embodiment which head is suitable for moving across a patient's skin during treatment.

In the discussion to this point, it has been assumed that the head utilized is applied to a point on a patient's skin where treatment is to be performed and that, after a suitable period of time has passed for cooling of the skin to the DE junction to have occurred, an optical radiation pulse, for example a laser pulse, is applied through the waveguide to treatment area 30. FIG. 10 shows an embodiment of the invention which, like the embodiments taught in application Ser. No. 09/078,055, is intended to be in contact with the patient's skin 18 and to be moved in direction 112 over the skin while remaining in contact therewith. Radiation applied to waveguides light paths 114 in this head may be continuous wave or may be pulsed at a high enough rate to permit movement of the head over the treatment area. For the embodiment shown in FIG. 10, the head has an area 116 ahead of waveguides 114 which passes over the treatment area before radiation is applied thereto. Region 116 is preferably of a thermally conductive material and is insulated from a second region 118 of the head, which is preferably also of a thermally conductive material, by a thermally insulating layer 120. A thermal electric element or other suitable heater/chiller 122 is in contact with portion 116 and may be used to either preheat or precool the treatment area. For example, if element 122 is a heater, it can heat the skin down to region 30 to a temperature below that at which thermal damage would occur. Further, a temperature sensor 124 is provided, for example up to 5 mm from the skin contacting surface (and preferably less, i.e., to 1 to 2 mm) to indicate skin temperature at for example the DE junction. Sensor 124, by detecting the heating of melanin in the epidermis provides an indication of skin type for the patient, which indication can be used to control the radiation applied. It also assures that overheating in the epidermis does not occur. A thermal electric element or other suitable cooler 126 connected to region 118 cools the epidermis ahead of waveguides 114 coming over a treatment area. A temperature sensor 128 can also be provided in region 118, for example up to 5 mm from the skin contacting surface, to assure that this region has cooled sufficiently before radiation is applied thereto and to protect against thermal damage to this region. While a single pair of waveguides 114 are shown in FIG. 10, typically a plurality of such waveguides would be stacked adjacent to each other in a direction into the figure. Two or more heaters/chillers 122, 126 could also be provided and two or more sensors 124, 128 could also be provided. Further, the sensor technology of this invention could also be utilized with other ones of the embodiments shown in application Ser. No. 09/078,055.

While the invention has been described above with reference to a particular system 10 and to particular head designs 16, neither are limitations on the invention. In particular, other techniques known in the art, for example circulating water or air, could be utilized for cooling waveguide 40 in lieu of thermoelectronic cooling elements 48, although such thermoelectronic cooling elements are at this time preferred. Some elements 48 (or other thermal control elements) might also be used to heat waveguide 40 to preheat the target area, after which either the same or different thermal control elements would be used to cool the waveguide as previously indicated to cool the patient's epidermis in the treatment area. A lens may also be substituted for waveguide 40, although waveguide 40 is currently preferred because of its superior thermal properties and its superior performance in retroreflection. Other light guiding/transmitting element may also be used and, in some applications, two or more such elements may be used as shown in FIG. 10, rather than a single element to transmit EM radiation through the head to the patient's skin. Other details of construction for head 16 or head 110 may also be varied, depending on application. Thus, while the invention has been particularly shown and described above with reference to preferred embodiments, the foregoing and other changes in form and detail may be made therein by one skilled in the art while still remaining within spirit and scope of the invention which is to be defined only by the appended claims.

What is claimed:

1. A head for applying EM radiation of a wavelength appropriate for treating a selected patient dermatologic problem to a selected volume of a patient's skin, the volume containing the problem to be treated, the head including:
   an optical waveguide;
   a light path for directing the EM radiation to a first end of the waveguide, said waveguide having a second end opposite said first end, said second end having a skin contacting surface;
   a temperature sensor at said second end of the waveguide and spaced by a distance $\Delta d$ from said skin contacting surface; and
   controls responsive to said temperature sensor for indicating of temperature at a selected depth below the patient's skin surface.

2. A head as claimed in claim 1 wherein $\Delta d$ is no more than 2 millimeters.

3. A head as claimed in claim 1 wherein $\Delta d$ is no more than 1 millimeter.

4. A head as claimed in claim 1 including a mechanism for removing heat from the waveguide.

5. A head as claimed in claim 4 wherein said mechanism includes a thermoelectric device having one side in thermal contact with said waveguide and an opposite side in thermal contact with a temperature sink.

6. A head as claimed in claim 1 wherein said head has a reflection aperture at a skin-contacting end thereof at least substantially as great as the aperture of radiation back-scattered from the patient's skin.

7. A head as claimed in claim 6 wherein said second end of the waveguide has an aperture at least substantially as great as the aperture of radiation back-scattered from the patient's skin.

8. A head as claimed in claim 6 wherein at least part of the back-scattered radiation enters said waveguide and is substantially internally reflected within said waveguide; and
   including a reflector within said waveguide for returning back-scattered radiation through the waveguide to the patient's skin.

9. A head as claimed in claim 8 wherein said reflector is at said first end of the waveguide.

10. A head as claimed in claim 9 wherein said reflector is also along at least a portion of waveguide sidewalls, and wherein said reflector has a coefficient of reflection at areas thereof such that backscattered radiation at angles nearer perpendicular to said skin contacting second end are reflected more strongly then back scattered radiation at angles nearer parallel to said second end.

11. A head as claimed in claim 6 including a reflector plate surrounding said waveguide at the second end thereof, the combined area of the plate and the waveguide projecting therethrough being substantially equal to the aperture of radiation back-scatter.

12. A head as claimed in claim 11 wherein said plate has a concave shape.

13. A head as claimed in claim 11 including a means for controlling the temperature of the plate.

14. A system for treating a selected dermatologic problem located in a selected volume of a patient's skin at a depth which is below the Dermal/Epidermal (DE) junction, comprising:

a source of EM radiation of a wavelength appropriate for treating said problem;

an optical waveguide having a first end at which said radiation is applied and a second end having a skin contacting surface for contacting the patient's skin, which second end is opposite said first end;

a temperature sensor at said second end of the waveguide, and spaced from said skin contacting surface by a distance Δd such that the temperature at said sensor is indicative of the temperature at a selected depth within the patient's skin;

a mechanism which removes heat from the patient's skin at least in the area thereof in contact with said waveguide; and controls operative in response to said sensor indicating that the patient's skin at said selected depth has been cooled to at least a selected temperature for permitting radiation from said source to be passed through said waveguide to the patient's skin, including said selected volume.

15. A system as claimed in claim 14 wherein said mechanism removes heat from the waveguide, the waveguide, when in contact with the skin, removing heat from, and thus cooling, the skin.

16. A system as claimed in claim 15 wherein said selected depth is the DE junction, and wherein said controls are operative in responsive to said sensor for maintaining the DE junction within a selected temperature range during application of said radiation to the patient's skin.

17. A system as claimed in claim 15 wherein said controls detect a temperature profile at said sensor, said profile being indicative of contact of said waveguide with the patient's skin, and wherein said controls prevent said radiation from passing to the patient's skin unless a predetermined profile is detected.

18. A system as claimed in claim 15 wherein said controls operate said mechanism to cool said waveguide to a desired temperature, and wherein said controls are responsive to said sensor for determining when said temperature has been reached.

19. A system as claimed in claim 14 wherein said sensor is located no more than a few millimeters from the skin contacting surface of said waveguide.

20. A system as claimed in claim 14 wherein said second end of the waveguide has an aperture at least substantially as great as the aperture of radiation back-scattered from the patient's skin.

21. A system as claimed in claim 20 wherein back-scattered radiation is substantially internally reflected within said waveguide; and including a reflector within said waveguide for returning back-scattered radiation through the waveguide to the patient's skin.

22. A system as claimed in claim 21 wherein said reflector is at said first end of the waveguide.

23. A system as claimed in claim 22 wherein said reflector is also along at least a portion of waveguide sidewalls, and wherein said reflector has a coefficient of reflection at areas thereof such that backscattered radiation at angles nearer perpendicular to said skin contacting second end are reflected more strongly then back scattered radiation at angles nearer parallel to said second end.

24. A system for treating a selected dermatologic problem located in a selected volume of a patient's skin at a depth d, which depth is below the Dermal/Epidermal (DE) junction, comprising:

a source of EM radiation of a wavelength appropriate for treating said problem;

an optical waveguide having a first end at which said radiation is applied and a second end for contacting the patient's skin, which second end is opposite said first end;

a mechanism which cools the patient's skin, at least in the portion thereof in contract with said waveguide, when said second end is in contact with the patient's skin;

a temperature sensor at said second end of the waveguide, the temperature at said sensor being indicative of the temperature at the patient's DE junction; and controls operative in response to the sensor sensing a selected increasing temperature profile at the sensor when the waveguide is placed in contact with the patient's skin for permitting radiation from said source to be passed through said waveguide to the patient's skin, including said selected volume.

25. A system as for treating a selected dermatologic problem located in a selected volume of a patient's skin, comprising:

a source of EM radiation of a wavelength appropriate for treating said problem;

an optical waveguide having a first end at which said radiation is applied and a second end for contacting the patient's skin, which second end is opposite said first end;

controls for selectively permitting radiation from said source to be passed through said waveguide to the patient's skin, including said selected volume;

said second end of the waveguide having an aperture at least substantially as great as the aperture of radiation back-scattered from the patient's skin, the back-scattered radiation being substantially internally reflected within said waveguide; and a reflector within said waveguide for returning back-scattered radiation through the waveguide to the patient's skin, wherein said reflector is at least at said first end of the waveguide.

26. A system as claimed in claim 25 wherein said reflector is also along at least a portion of waveguide sidewalls, and wherein said reflector has a coefficient of reflection at areas thereof such that backscattered radiation at angles nearer perpendicular to said skin contacting second end are reflected more strongly then back scattered radiation at angles nearer parallel to said second end.

27. A head for applying EM radiation of a wavelength appropriate for treating a selected patient dermatologic problem at a selected volume of a patient's skin, the head comprising:

an optical waveguide;

a light path for directing the EM radiation to a first end of the waveguide, said waveguide having a skin-contacting second end which is opposite said first end;

some of the radiation passing through the waveguide to a patient's skin being back-scattered over a back-scatter aperture, said second end of the waveguide being at least part of a reflection aperture at least substantially as great as said back-scatter aperture, back-scattered radiation entering the waveguide being substantially internally reflected within said waveguide; and a reflector within said waveguide for returning the back-scattered radiation entering the waveguide through the waveguide to the patient's skin.

28. A head as claimed in claim 27 wherein said reflector is also along at least a portion of waveguide sidewalls, and wherein said reflector has a coefficient of reflection at areas thereof such that backscattered radiation entering the waveguide at angles nearer perpendicular to said skin contacting second end are reflected more strongly then back scattered radiation entering at angles nearer parallel to said second end.

29. A head as claimed in claim 27 wherein said waveguide is cooled, and means for maintaining a moisture-free environment for said reflector to inhibit condensation thereon, wherein said reflector is at least at said first end of the waveguide.

30. A head as claimed in claim 27 wherein said second end of the waveguide has an aperture at least substantially as great as the aperture of radiation back-scattered from the patient's skin.

31. A head as claimed in claim 27 including a reflector plate surrounding said waveguide at the second end thereof, the combined area of the plate and the waveguide projecting therethrough being substantially equal to the aperture of radiation back-scatter.

32. A head as claimed in claim 31 wherein said plate has a concave shape.

33. A head as claimed in claim 31 including a means for controlling the temperature of the plate.

34. A head for applying EM radiation of a wavelength appropriate for treating a selected patient dermatologic problem at a selected volume of a patient's skin, the head comprising:
a skin-contacting surface at least a portion of which is formed as a reflection plate;
at least one light path passing through said head and terminating at said skin-contacting surface, said EM radiation being applied through said at least one light path to the patient's skin;
some of the radiation passing through the waveguide to a patient's skin being back-scattered over a back-scatter aperture, said reflection plate being at least part of reflection means for returning back-scattered radiation to the patient's skin, said reflection means having a reflection aperture at least substantially as great as said back-scatter aperture.

35. A head for applying EM radiation of a wavelength appropriate for treating a selected patient dermatologic problem at a selected volume of a patient's skin, the head comprising:
at least on optical waveguide for receiving said EM radiation and for directing it to a skin-contacting surface of the at least one waveguide;
a standoff having a first and second end, the first end surrounding said at least one waveguide at its lower end and forming a substantially air-tight seal therewith, and said second end being adapted to contact the patient's skin over said selected volume to form a chamber between said skin-contacting waveguide surface, the patient's skin and walls of the standoff;
and means for creating negative pressure in said chamber to draw the patient's skin therein and into contact with said skin-contacting surface.

36. A head as claimed in claim 35 wherein the walls of said standoff are reflective to return back-scattered radiation to the patient's skin.

37. A head as claimed in claim 35 wherein said means for creating negative pressure includes a hose mounted at one end to open into said chamber and connected at its other end to a source of negative pressure.

38. A head as claimed in claim 35 wherein said means for creating negative pressure includes the walls of said standoff being deformable when pressure is applied to the waveguide to permit the skin-contacting surface of the waveguide to contact the patient's skin, forcing most of the air from said chamber, said walls returning to their undeformed state when pressure is released resulting in the creation of negative pressure in said chamber.

39. A head as claimed in claim 38 wherein said walls of the standoff are in the form of a bellows.

40. A head as claimed in claim 38 wherein said walls of the standoff are in the form of a suction cup.

41. A head as claimed in claim 38 wherein said walls of the standoff are in the form of a elastic ring.

42. A head for applying EM radiation of a wavelength appropriate for treating a selected patient dermatologic problem at a selected volume of a patient's skin, the head comprising:
at least one first optical waveguide for receiving said EM radiation and for directing it to a output surface of the at least one waveguide; and
a second optical waveguide having a first surface mounted to the output surface of the first optical waveguide to receive said EM radiation therefrom and having a second skin-contacting surface opposite said first surface, said skin-contacting surface having a larger area than said output surface and said second waveguide being formed to provide a larger optical aperture than that of said first waveguide, said second optical waveguide including a reflector mechanism which returns to the patient's skin radiation back-scattered therefrom.

43. A head as claimed in claim 42 wherein the ratio of the spacing between said first and second surfaces of the second waveguide and a selected surface dimension of said second surface is approximately 1.5 to 1.0.

44. A head as claimed in claim 42 wherein said selected surface dimension is one of the length of a side of said second surface and a diameter of said second surface.

45. A head as claimed in claim 44 wherein said means for reflecting including forming at least a portion of said first surface so as to reflect radiation impinging thereon.

46. A head as claimed in claim 45 wherein said reflector is also along at least a portion of waveguide sidewalls, and wherein said reflector has a coefficient of reflection at areas thereof such that backscattered radiation entering the waveguide at angles nearer perpendicular to said skin contacting surface are reflected more strongly then back scattered radiation entering at angles nearer parallel to said skin contacting surface.

47. A head for applying EM radiation of a wavelength appropriate for treating a selected patient dermatologic problem at a selected volume of a patient's skin, the head comprising:
a skin-contacting surface;
at least one light path passing through said head and terminating at said skin-contacting surface, said EM radiation being applied through said at least one light path to the patient's skin;
temperature sensor located in said head and spaced by a distance $\Delta d$ from said skin contacting surface; and controls responsive to said temperature sensor for indicating of temperature at a selected depth below the patient's skin surface.

48. A head as claimed in claim 47 wherein said head is moved across a patient's skin during treatment, and including a head portion of a thermally conductive material passing over the skin prior to said at least one light path, a said temperature sensor being located in said head portion within less than 5 mm of said skin contacting surface.

49. A head as claimed in claim 48 including means for one of heating and cooling said head portion to preheat/precool the patient skin prior to application of EM radiation thereto.

50. A head as claimed in claim 48 including means for heating said head portion to preheat the patients skin prior to application of EM radiation thereto, and means for utilizing the output of said temperature sensor in response to the preheating to determine patient skin type.

* * * * *